United States Patent
Fan et al.

(10) Patent No.: US 7,812,033 B2
(45) Date of Patent: *Oct. 12, 2010

(54) METHOD FOR INCREASING THE ACTIVITY OF ACID-β-GALACTOSIDASE

(75) Inventors: Jian-Qiang Fan, Demarest, NJ (US); Satoshi Ishii, Omichi-machi (JP); Naoki Asano, Kotatsuno (JP)

(73) Assignee: Mount Sinai School of Medicine of New York University, New York, NY (US)

( * ) Notice: Subject to any disclaimer, the term of this patent is extended or adjusted under 35 U.S.C. 154(b) by 410 days.

This patent is subject to a terminal disclaimer.

(21) Appl. No.: 11/528,903

(22) Filed: Sep. 27, 2006

(65) Prior Publication Data

US 2007/0021381 A1  Jan. 25, 2007

Related U.S. Application Data

(63) Continuation of application No. 10/989,258, filed on Nov. 16, 2004, now Pat. No. 7,141,582, which is a continuation of application No. 10/304,395, filed on Nov. 26, 2002, now Pat. No. 6,916,829, which is a continuation of application No. 09/948,348, filed on Sep. 7, 2001, now Pat. No. 6,599,919, which is a continuation of application No. 09/604,053, filed on Jun. 26, 2000, now Pat. No. 6,583,158, which is a continuation-in-part of application No. 09/087,804, filed on Jun. 1, 1998, now Pat. No. 6,274,597.

(51) Int. Cl.
A61K 31/445 (2006.01)
(52) U.S. Cl. ....................... 514/315; 435/208
(58) Field of Classification Search ........................ None
See application file for complete search history.

(56) References Cited

U.S. PATENT DOCUMENTS

| 4,639,436 | A | 1/1987 | Junge et al. |
|---|---|---|---|
| 5,030,628 | A | 7/1991 | Partis et al. |
| 5,030,638 | A | 7/1991 | Partis et al. |
| 5,043,273 | A | 8/1991 | Scudder et al. |
| 5,051,407 | A | 9/1991 | Boshegan et al. |
| 5,192,772 | A | 3/1993 | Yoshikuni et al. |
| 5,250,545 | A | 10/1993 | Tsuroka et al. |
| 5,292,750 | A | 3/1994 | Yoshikuni et al. |
| 5,399,567 | A | 3/1995 | Platt et al. |
| 5,504,078 | A | 4/1996 | Ducep et al. |
| 5,561,221 | A | 10/1996 | Yoshida et al. |
| 5,580,884 | A | 12/1996 | Platt et al. |
| 5,596,005 | A | 1/1997 | Wong et al. |
| 5,622,972 | A | 4/1997 | Bryant et al. |
| 5,643,888 | A | 7/1997 | Rorschneider |
| 5,656,641 | A | 8/1997 | Platt et al. |
| 5,691,306 | A | 11/1997 | Bergeron et al. |
| 5,786,368 | A | 7/1998 | Platt et al. |
| 5,798,366 | A | 8/1998 | Platt et al. |
| 5,801,185 | A | 9/1998 | Platt et al. |
| 5,844,102 | A | 12/1998 | Sierks et al. |
| 5,863,903 | A | 1/1999 | Lundgren et al. |
| 5,981,494 | A | 11/1999 | Rademacher et al. |
| 6,177,447 | B1 | 1/2001 | Aerts |
| 6,210,666 | B1 | 4/2001 | Miyamura |
| 6,225,325 | B1 | 5/2001 | Jacob |
| 6,274,597 | B1 | 8/2001 | Fan et al. |
| 6,291,657 | B1 | 9/2001 | Platt et al. |
| 6,465,488 | B1 | 10/2002 | Butters et al. |
| 6,583,158 | B1 * | 6/2003 | Fan et al. ..................... 514/315 |
| 6,589,964 | B2 * | 7/2003 | Fan et al. ..................... 514/315 |
| 6,599,919 | B2 * | 7/2003 | Fan et al. ..................... 514/315 |
| 6,774,135 | B2 | 8/2004 | Fan et al. |
| 6,916,829 | B2 * | 7/2005 | Fan et al. ..................... 514/315 |
| 7,174,582 | B1 | 11/2006 | Fan et al. |
| 7,514,453 | B2 | 4/2009 | Fan et al. |
| 2001/0018090 | A1 | 8/2001 | Noda et al. |
| 2001/0044453 | A1 | 11/2001 | Jacob et al. |
| 2002/0006909 | A1 | 1/2002 | Perlmutter et al. |
| 2002/0095135 | A1 | 7/2002 | Meeker et al. |
| 2002/0115667 | A1 | 8/2002 | Walkley et al. |
| 2004/0242539 | A1 | 12/2004 | Fan et al. |

FOREIGN PATENT DOCUMENTS

| CA | 2278507 | 7/1998 |
|---|---|---|
| JP | 61-280472 | 6/1985 |
| WO | WO 87/03903 | 7/1987 |
| WO | WO 92/00277 | 4/1993 |
| WO | WO 95/19172 | 7/1995 |
| WO | WO 99/24401 | 5/1999 |
| WO | WO 99/40435 | 8/1999 |
| WO | WO 99/62517 | 12/1999 |
| WO | WO 00/29556 | 5/2000 |
| WO | WO 00/32175 | 6/2000 |
| WO | WO 00/33843 | 6/2000 |
| WO | WO 00/56334 | 9/2000 |
| WO | WO 00/62799 | 10/2000 |
| WO | WO 01/02862 | 1/2001 |

(Continued)

OTHER PUBLICATIONS

Tropak and Mahuran, "Lending a helping hand, screening chemical libraries for compounds that enhance beta-hexosaminidase A activity in GM2 gangliosidosis cells", FEBS Journal 274: 4951-4961 (2007).*

(Continued)

*Primary Examiner*—Anand U Desai
(74) *Attorney, Agent, or Firm*—Baker Botts LLP

(57) ABSTRACT

Method for enhancing in a mammalian cell the activity of an enzyme associated with Gaucher Disease by administering a competitive inhibitor of glucocerebrosidase in an amount effective to enhance the activity of the enzyme. Preferred compounds for use in the method are imino sugars and related compounds. In particular, C8-12-alkyl derivatives of N-alkyl-deoxynojirimycin, isofagomine compounds, and calystegine compoiunds are effective to enhance glucocerebrosidase activity.

4 Claims, 17 Drawing Sheets

FOREIGN PATENT DOCUMENTS

| | | |
|---|---|---|
| WO | WO 01/07078 | 2/2001 |
| WO | WO 01/10429 | 2/2001 |
| WO | WO 01/21652 | 3/2001 |
| WO | WO 94/26714 | 9/2001 |
| WO | WO 02/28348 | 4/2002 |

OTHER PUBLICATIONS

Naoki Asano, et al., "In Vitro inhibition and intracellular enhancement of lysosmal α-galactosidase A by deoxygalactonojirimycin and its derivatives," Eur. J. Biochem 2000; vol. 267, pp. 4179-4186.

Naoki Asano et al., "Specific alpha galactosidase inhibitors, N-methylcalystegines-structure/activity relationships of calystegines from *Lycium chinense*," Eur. J. Biochem., vol. 248: 296-303, 1997.

Naoki Asano et al., "Homojirimycin isomers and glycosides from *Aglaonema treubii*," J. Nat. Prod. 1997; vol. 60, p. 98.

Naoki Asano et al., "Nitrogen-in-the-ring pyranoses and furanoses: structural basis of inhibition of mammalian glycosidases," J. Med. Chem. 1994; vol. 37, pp. 3701.

Bernotas et al., "Synthesis of (+)-1, 5-dideoxy-1,5-imino-D-galactitol, a potent alpha galactosidase inhibitor," Carbohydrate Res., vol. 167: 306-311, Sep. 1987.

C. Randall Brown, et al., "Chemical chaperones correct the mutant phenotype of the F508 cystic fibrosis transmembrane conductance regulator protein," Cell Stress & Chaperones 1996; vol. 1 No. 2, pp. 117-125.

Jon A. Burrows et al., "Chemical chaperones mediate increased secretion of mutant α1-antitrypsin (α1-AT) Z: A potential pharmacological strategy for prevention of liver injury and emphysema in α1-AT deficiency," Proc. Natl. Acad. Sci. U.S.A. 2000; vol. 97, No. 4, pp. 1796-1801.

M.P. Dale et al., "Reversible inhibitors of beta-glucosidase," Biochemistry 1985; vol. 24, pp. 3530-3539.

Jian-Qiang Fan, et al., "Accelerated transport and maturation of lysosomal α-galactosidase A in Fabry lymphoblasts by an enzyme inhibitor," Nature Medicine 1999; vol. 5, No. 1, pp. 112-115.

Barbara A. Foster, et al., "Pharmacological Rescue of mutant p53 conformation and function," Science 1999; vol. 286, pp. 2507-2510.

Goldmann et al., "Biological activities of the nortropane alkaloid, calystegine B2, and analogs: structure function relationships," J. Natl. Prod., vol. 59, pp. 1137-1142, 1996.

A. M Hurtley and A. Helenius, "Protein oligomerization in the endoplasmic reticulum," Annu. Rev. Cell Biol. 1989; vol. 5, pp. 277-307.

Ishii et al., "Characterization of a mutant α-galactosidase gene product for the late-onset cardiac form of Fabry disease," Biochem. Biophys. Res. Comm. 1993; 197(3):1585-89.

Galina Kuznetsov, et al., "Folding of secretory and membrane proteins," New Engl. J. Med. 1998; vol. 339, No. 23, pp. 1688-1695.

Legler et al., "Synthesis of 5-amino-5-deoxy-D-galactopyranose and 1,5-dideoxy-1,5-imino-D-galactitol, and their inhibition of alpha and beta-D-galactosidases," Carbohydrate Research, vol. 155, pp. 119-129, Nov. 1986.

Tip W. Loo, et al., "Correction of defective protein kinesis of human P-glycoprotein mutants by substrates and modulators," J. Biol. Chem. 1997; vol. 272, No. 2, pp. 709-712.

Jean-Pierre Morello, et al., "Pharmacological chaperones rescue cell-surface expression and functions of misfolded V2 vasopressin receptor mutants," J. Clin. Invest. 2000; vol. 105, pp. 887-895.

Okumiya et al., Genetic Disease 1998; 2(1):76-82 (Japanese).

Okumiya et al., "Galactose stabilizes various missense mutants of alpha-galactosidase in Fabry disease," Biochem. Biophys. Res. Comm. 1997; vol. 214, pp. 1219-1224.

Okumiya e al., Biochem. Biophys. Res. Comm. 1995; 214(3): 1219-24.

Jean-Pierre Morello, et al., "Pharmacological chaperones: a new twist on receptor folding," TiPS, 2000; vol. 21, pp. 466-469.

Ulla E. Petaja-Repo et al., "Ligands act as pharmacological chaperones and increase the efficiency of σ opioid receptor maturation," The EMBO J. 2002; 21(7):1628-37.

F.M. Platt et al., "Prevention of lysosomal storage in Tay-Sachs mice treated with N-butyldeoxynojirimycin," Science 1997; vol. 276, pp. 428-431.

Frances M. Platt, et al., "N-butyldeoxynojirimycin is a novel inhibitor of glycolipid biosynthesis," J. Biol. Chem. 1994; vol. 269, No. 11, pp. 8362-8365.

Frances M. Platt et al., "N-butyldeoxygalactonorjirimycin inhibits glycolipid biosynthesis but does not affect N-linked oligosaccharide processing," J. Biol. Chem. 1994; vol. 269, No. 43, pp. 27108-27114.

Pobojewski et al., "Experimental drug reverses effects of Fabry disease," The University Record (Univ. of Michigan), vol. 55, No. 34, p. 11, Jun. 2000.

Ronald C. Rubenstein, et al., In vitro pharmacologic restoration of CFTR-mediated chloride transport with sodium 4-phenylgutyrate in cystic fibrosis epithelial cells containing F508-CFTR,@ Pharmacologic Correction of F508-CFTR 1997; vol. 100, No. 10, pp. 2457-2464.

Sue Wicker, et al., "Posttranslational quality control: folding, refolding, and degrading proteins," Science 1999; vol. 286, pp. 1888-1893.

Zhou et al., A Correction of defective protein trafficking of a mutant HERG potassium channel in human Long QT syndrome, J. Biol. Chem. 1999; 274(44):31123-31126.

Hideki Sakahira, et al., "Specific chaperone-like activity of inhibitor of caspase-activated DNase for caspase-activated DNase," J. Biol. Chem. 2000, vol. 275, No. 11, pp. 8091-8096.

Ruvinov et al., Monovalent Cations Partially Repair a Conformational Defect in a Mutant Tryptophan Synthase α2 β2 Complex (β-E109A)*; J. Biol. Chem. 1995; 270: 17333-38.

Asano et al., "Nitrogen-containing furanose and pyranose analogues from *Hyacinthus orientalis*," *J Nat Prod*. (1998);61(5):625-8.

Asano et al., "Homojirimycin isomers and N-alkylated homonojirimycins: structural and conformational basis of inhibition of glycosidases," *J Med Chem*. (1998);41(14):2565-71.

Ohshima et al., "alpha-Galactosidase A deficient mice: a model of Fabry disease," *Proc Natl Acad Sci U S A*. (1997);94(6):2540-4.

Ishii et al., "Role of Ser-65 in the activity of alpha-galactosidase A: characterization of a point mutation (S65T) detected in a patient with Fabry disease," *Arch Biochem Biophys*. (2000);15;377(2):228-33.

Asano et al., "Homojirimycin Isomers and Glycosides from *Aglaonema treubii*," J. Nat. Prod., (1997);60 (2):98-101.

* cited by examiner

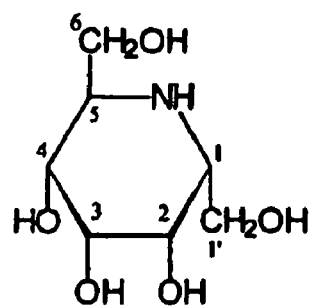
FIG. 2 A
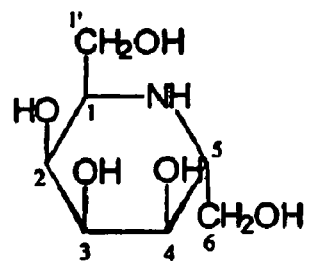
FIG. 2 B
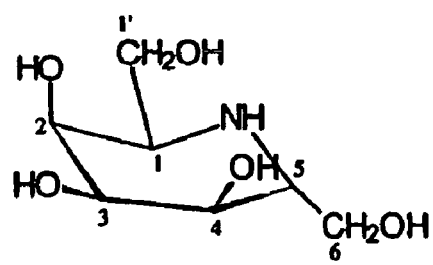
FIG. 2 C
FIG. 2 D
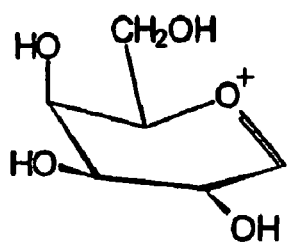

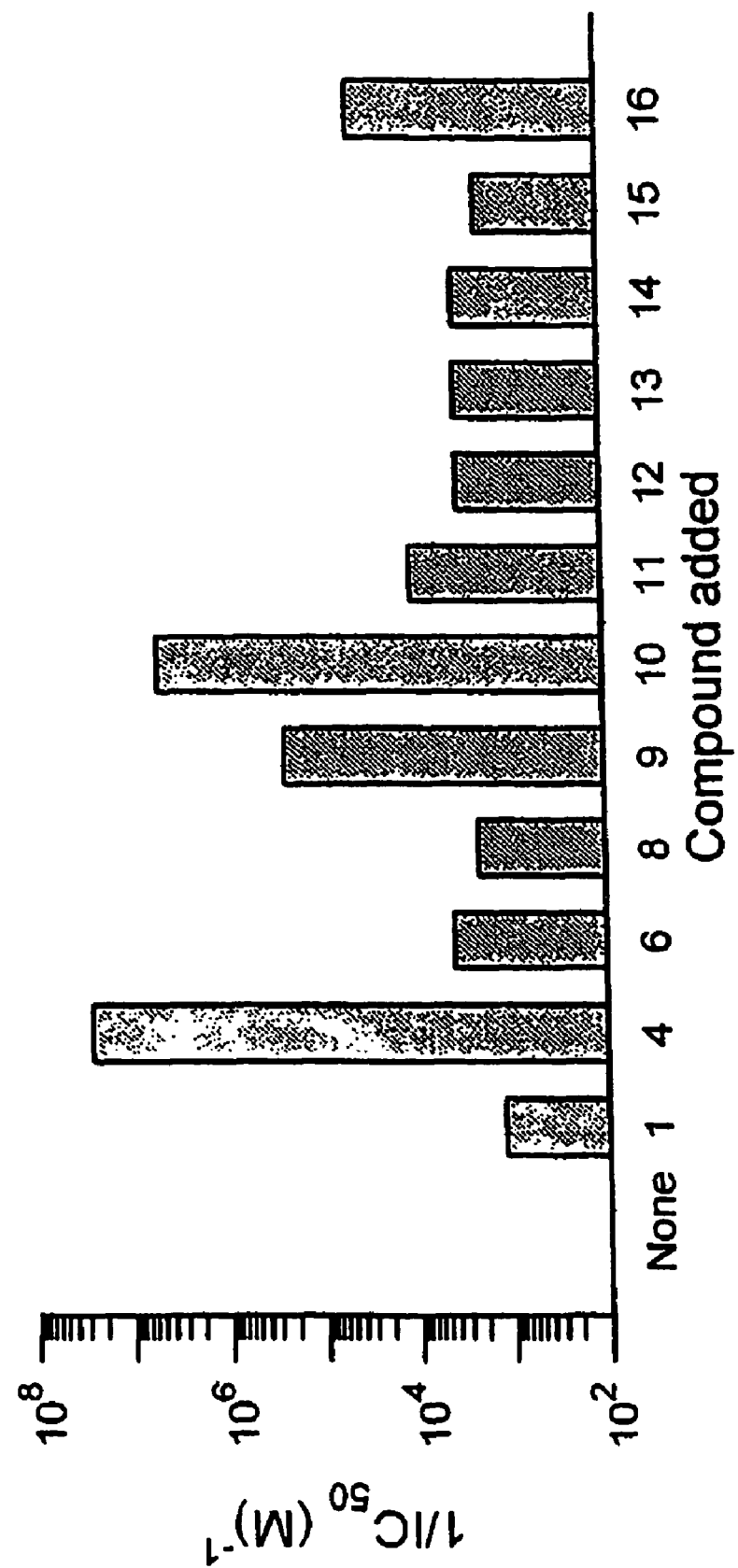

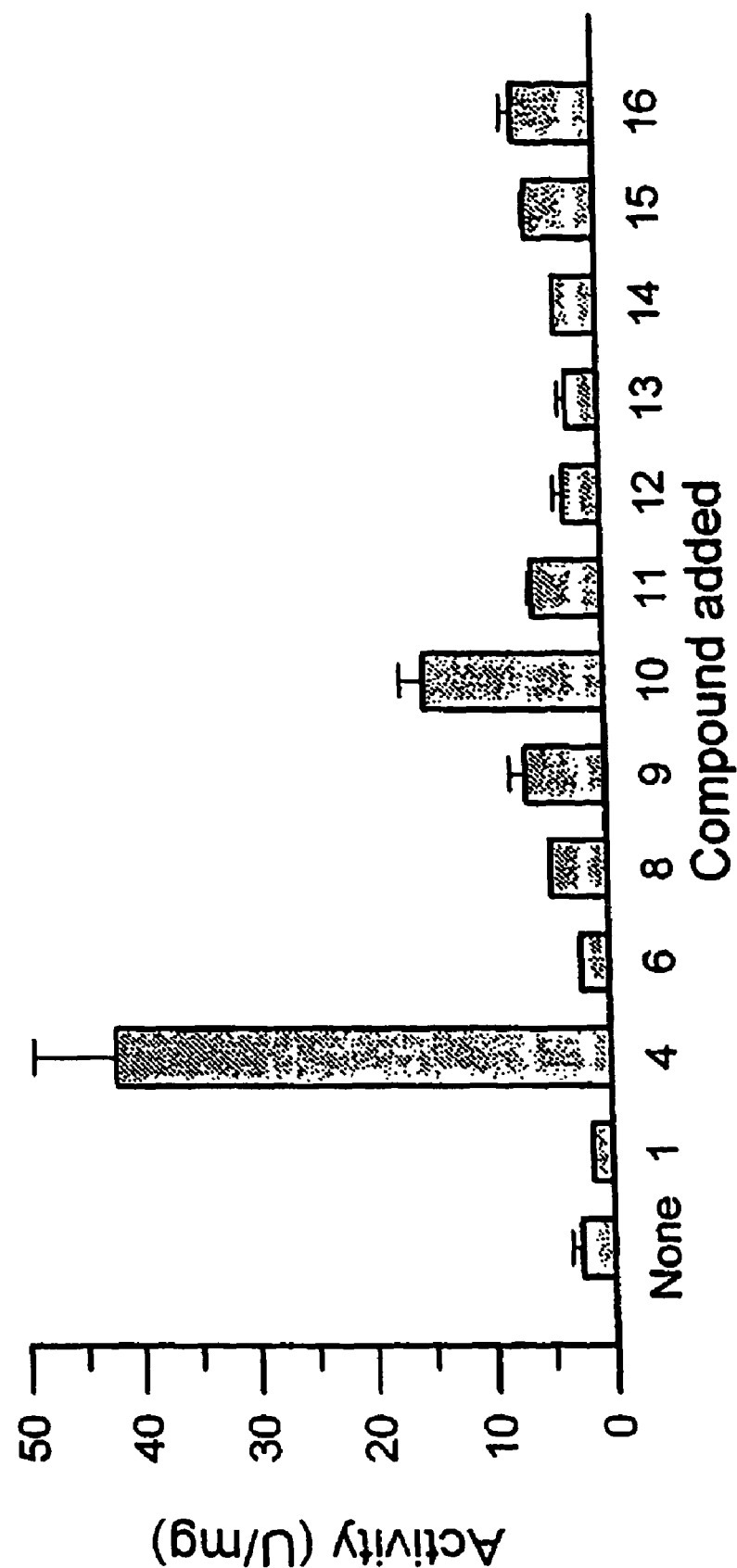

FIG. 12
Conventional iminosugars:
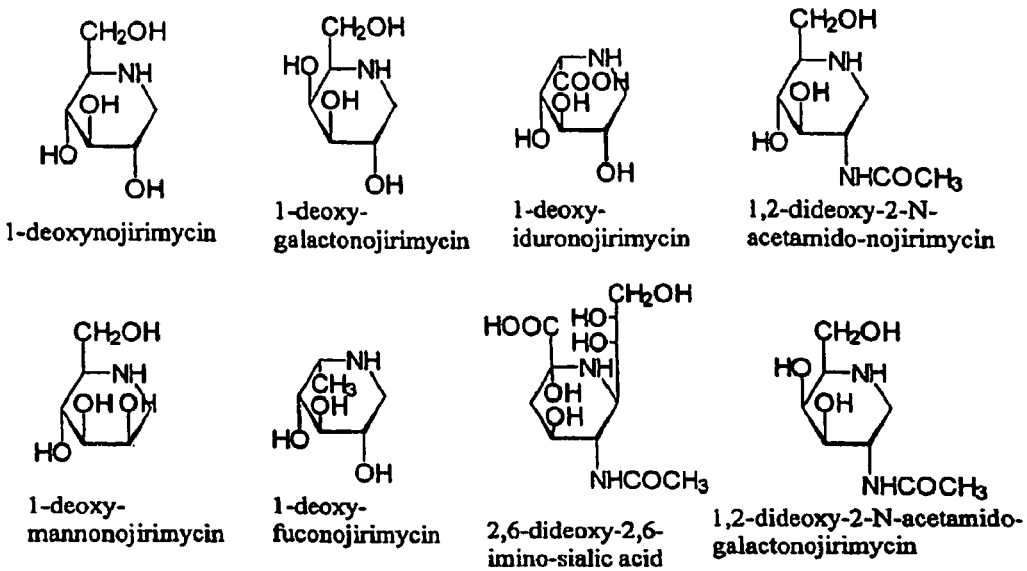
1-N-iminosugars:
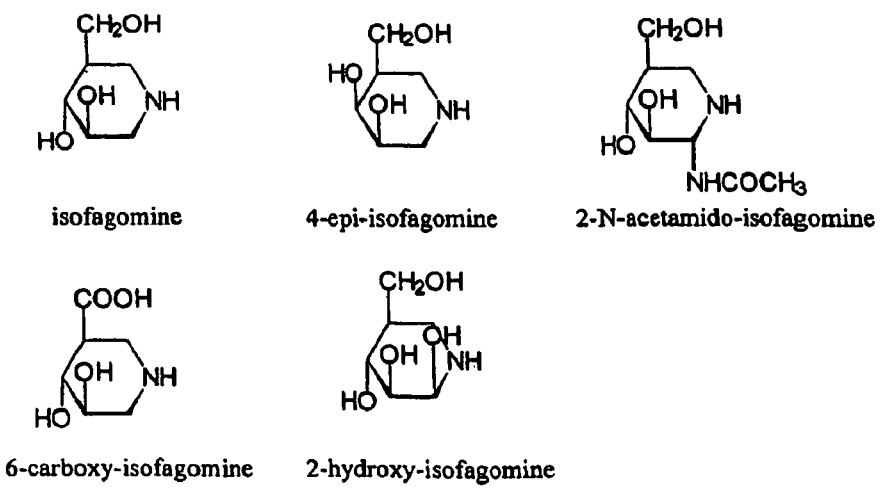

METHOD FOR INCREASING THE ACTIVITY OF ACID-β-GALACTOSIDASE

CROSS-REFERENCE TO RELATED APPLICATIONS

This application is a continuation of application Ser. No. 10/989,258, filed on Nov. 16, 2004, now U.S. Pat. No. 7,141,582, which is a continuation of application Ser. No. 10/304,395, filed on Nov. 26, 2002, now U.S. Pat. No. 6,916,829, which is a continuation of application Ser. No. 09/948,348, filed on Sep. 7, 2001, now U.S. Pat. No. 6,599,919, which is a continuation of application Ser. No. 09/604,053, filed on Jun. 26, 2000, now U.S. Pat. No. 6,583,158, which is a continuation-in-part of application Ser. No. 09/087,804, filed on Jun. 1, 1998, now U.S. Pat. No. 6,274,597. Each of these prior references are hereby incorporated herein by reference in their entireties.

BACKGROUND OF THE INVENTION

1. Field of the Invention

This invention relates to a method of enhancing mutant enzyme activities in lysosomal storage disorders by administration of competitive inhibitors of the enzymes, in particular imino sugars and related compounds.

2. Background Information

Proteins are synthesized in the cytoplasm, and the newly synthesized proteins are secreted into the lumen of the endoplasmic reticulum (ER) in a largely unfolded state. In general, protein folding is an event governed by a principle of self assembly. The tendency of proteins to fold into their native (active) conformation is contained in their amino acid sequences (1). In vitro, the primary structure folds into secondary structures of α-helices and β-sheets coupled with hydrophobic collapse in the formation of a biologically active tertiary structure which also gains increased conformational stability. However, the folding of protein in vivo is rather complicated, because the combination of ambient temperature and high protein concentration stimulates the process of aggregation, in which amino acids normally buried in the hydrophobic core interact with their neighbours non-specifically. To avoid this problem, protein folding is usually facilitated by a special group of proteins called molecular chaperones which prevent nascent polypeptide chains from aggregating, and bind to protein so that the protein refolds in the active state (2).

Molecular chaperones are present in virtually all types of cells and in most cellular compartments. Some are involved in the transport of proteins and in supporting cells to survive under stresses such as heat shock and glucose starvation. Among the molecular chaperones (3-6), BIP (immunoglobulin heavy-chain binding protein, Grp78) is the best characterized chaperone of the ER (7). Like other molecular chaperones, BIP interacts with many secretory and membrane proteins within the ER throughout their maturation, although the interaction is normally weak and short-lived when the folding proceeds smoothly. Once the native protein conformation is achieved, the molecular chaperone no longer binds. However, the interaction between BIP and those proteins that fail to fold, assemble or be properly glycosylated becomes stable, and usually leads to degradation of these proteins through the ubiquitin pathway. This process serves as a "quality control" system in the ER which ensures that only properly folded and assembled proteins are transported to the Golgi complex for further maturation, and those improperly folded proteins are retained for subsequent degradation (8).

In many hereditary disorders, mutant gene products are structurally altered and may not fold correctly, signalling the quality control system to retain and degrade them in situ. This process may contribute significantly to the protein deficiency, although the function of the protein may have been only partially impaired (9-12). For example, the most common mutation in cystic fibrosis, a deletion of phenylalanine-508 (ΔF508) in the CFTR protein which functions as a chloride channel in the plasma membrane, results in misfolding and retardation of the ΔF508-CFTR protein in the ER, and subsequent degradation by the cytosolic proteasome system (13-14), even though it retains almost full biologic activity when inserted into plasma membranes (15). The list of diseases caused by mutations that alter protein folding is increasing, and it includes $\alpha_1$-antitrypsin deficiency (16-17), familial hypercholesterolemia (18), Alzheimer's disease (18a), Marfan syndrome (19), osteogenesis imperfecta (20), carbohydrate-deficient glycoprotein syndrome (21), and Maroteaux-Lamy syndrome (22).

Lysosomal storage disorders are a group of diseases resulting from the abnormal metabolism of various substrates, including glycosphingolipids, glycogen, mucopolysaccharides and glycoproteins. The metabolism of exo- and endogenous high molecular weight compounds normally occurs in the lysosomes, and the process is normally regulated in a stepwise process by degradation enzymes. Therefore, a deficient activity in one enzyme may impair the process, resulting in an accumulation of particular substrates. Most of these diseases can be clinically classified into subtypes: i) infantile-onset; ii) juvenile-onset; or iii) late-onset. The infantile-onset forms are often the most severe usually with no residual enzyme activity. The later-onset forms are often milder with low, but often detectable residual enzyme activity. The severity of the juvenile-onset forms are in between the infantile-onset and late-onset forms. Table 1 contains a list of a number of known lysosomal storage disorders and their associated defective enzymes. In the adult-onset forms of lysosomal storage disorders listed in Table 1, certain mutations cause instability of the encoded protein.

TABLE 1

Lysosomal storage disorders.

| Lysosomal storage disorder | Defective enzyme |
|---|---|
| Pompe disease | Acid α-glucosidase |
| Gaucher disease | Acid β-glucosidse, or glucocerebrosidase |
| Fabry disease | α-Galactosidase A |
| $G_{M1}$-gangliosidosis | Acid β-galactosidase |
| Tay-Sachs disease | β-Hexosaminidase A |
| Sandhoff disease | β-Hexosaminidase B |
| Niemann-Pick disease | Acid sphingomyelinase |
| Krabbe disease | Galactocerebrosidase |
| Farber disease | Acid ceramidase |
| Metachromatic leukodystrophy | Arylsulfatase A |
| Hurler-Scheie disease | α-L-Iduronidase |
| Hunter disease | Iduronate-2-sulfatase |
| Sanfilippo disease A | Heparan N-sulfatase |
| Sanfilippo disease B | α-N-Acetylglucosaminidase |
| Sanfilippo disease C | Acetyl-CoA: α-glucosaminide N-acetyltransferase |
| Sanfilippo disease D | N-Acetylglucosamine-6-sulfate sulfatase |
| Morquio disease A | N-Acetylgalactosamine-6-sulfate sulfatase |
| Morquio disease B | Acid β-galactosidase |
| Maroteaux-Lamy disease | Arylsulfatase B |
| Sly disease | β-Glucuronidase |
| α-Mannosidosis | Acid α-mannosidase |
| β-Mannosidosis | Acid β-mannosidase |
| Fucosidosis | Acid α-L-fucosidase |

TABLE 1-continued

Lysosomal storage disorders.

| Lysosomal storage disorder | Defective enzyme |
|---|---|
| Sialidosis | Sialidase |
| Schindler-Kanzaki disease | α-N-acetylgalactosaminidase |

In their earlier filed patent application (U.S. application Ser. No. 09/087,804), the present inventors proposed a novel therapeutic strategy for Fabry disease, a lysosomal storage disorder caused by deficient lysosomal α-galactosidase A (α-Gal A) activity in which certain mutations encoded mutant proteins which have folding defects. The application presented evidence demonstrating that 1-deoxygalactonojirimycin (DGJ), a potent competitive inhibitor of α-Gal A, effectively increased in vitro stability of a mutant α-Gal A (R301Q) at neutral pH and enhanced the mutant enzyme activity in lymphoblasts established from Fabry patients with the R301Q or Q279E mutations. Furthermore, oral administration of DGJ to trangenic mice overexpressing a mutant (R301Q) α-Gal A substantially elevated the enzyme activity in major organs (24).

The principle of this strategy is as follows. Since the mutant enzyme protein appears to fold improperly in the ER where pH is neutral, as evidenced by its instability at pH 7 in vitro (25), the enzyme protein would be retarded in the normal transport pathway (ER→Golgi apparatus→endosome→lysosome) and subjected to rapid degradation. In contrast, an enzyme protein with a proper folding conformation could be efficiently transported to the lysosomes and remain active, because the enzyme is more stable below pH 5. Therefore, a functional compound which is able to induce a stable molecular conformation of the enzyme is expected to serve as a "chemical chaperone" for the mutant protein to stabilize the mutant protein in a proper conformation for transport to the lysosomes. Some inhibitors of an enzyme are known to occupy the catalytic center of enzyme, resulting in stabilization of its conformation in vitro, they may also serve as "chemical chaperones" to enforce the proper folding of enzyme in vivo, thus rescue the mutant enzyme from the ER quality control system. It is noted that while this is believed to be the mechanism of operation of the present invention, the success of the invention is not dependent upon this being the correct mechanism.

SUMMARY OF THE INVENTION

The present inventors have unexpectedly found that potent competitive inhibitors for enzymes associated with lysosomal storage disorders enhance the activity of such enzymes in cells when administered at concentrations lower than that normally required to inhibit the intracellular enzyme activity. The effect is particularly significant on certain defective or mutant enzymes, but also occurs in cells containing the normal enzyme type.

Accordingly, it is one object of the present invention to provide a method of preventing degradation of mutant enzymes associated with lysosomal storage diseases in mammalian cells, particularly in human cells.

It is a further object of the invention to provide a method of enhancing the activity of enzymes associated with lysosomal storage disease in mammalian cells, particularly in human cells. The method of the present invention enhance the activity of both normal and mutant α-Gal A, particularly of mutant α-Gal A which is present in certain forms of Fabry disease.

The methods of the present invention also enhance the activity of certain mutant β-galactosidase and glucocerebrosidase and are expected to be useful in other lysosomal storage diseases, including those listed in Table 1.

In addition, the methods of the invention are also expected to be useful in nonmammalian cells, such as, for example, cultured insect cells and CHO cells which are used for production of α-Gal A for enzyme replacement therapy.

It is yet a further object of the invention to provide a method of treatment for patients with lysosomal storage disorders such as those listed in Table 1.

Compounds expected to be particularly effective for Fabry disease in the methods of the invention are galactose and glucose derivatives having a nitrogen replacing the oxygen in the ring preferably galactose derivatives such as 1-deoxygalactonojirimycin and 4-epi-α-homonojirimycin. The term "galactose derivative" is intended to mean that the hydroxyl group at the C-3 position is equatorial and the hydroxyl group at the C-4 position is axial, as represented, for example, by the following structures:

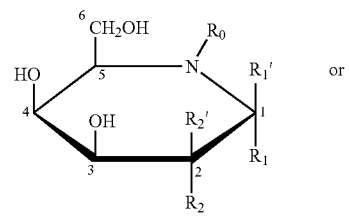

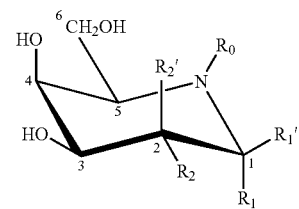

wherein $R_0$ represents H, methyl or ethyl; $R_1$ and $R_1'$ independently represent H, OH, a 1-4 carbon alkyl, alkoxy or hydroxyalkyl group (e.g., $CH_2OH$); $R_2$ and $R_2'$ independently represent H, OH or alkyl group (n=1-8).

Other specific competitive inhibitors for α-galactosidase, such as for example. calystegine $A_3$ and $B_2$, and N-methyl derivatives of these compounds should be useful in the method of the invention. The calystegine compounds can be represented by the formula

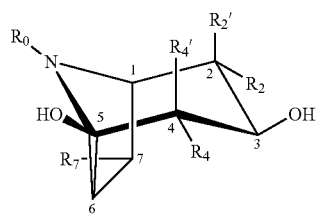

wherein for calystegine $A_3$: $R_0$=H, $R_2$=$R_2'$=H, $R_4$=OH. $R_4'$=$R_7$=H; for calystegine $B_2$: $R_0$=H. $R_2$=OH, $R_2'$=$R_4'$=H, $R_4$=OH, $R_7$=H; for N-methyl-calystegine $A_3$: $R_0$=$CH_3$, $R_2$=$R'$=H. $R_4$=OH, $R_4'$=$R_7$=H; for N-methyl-calystegine $B_2$: $R_0$=$CH_3$, $R_2$=OH, $R_2'$=$R_4'$=H. $R_4$=OH. $R_7$=H.

Administration of a pharmaceutically effective amount of a compound of formula

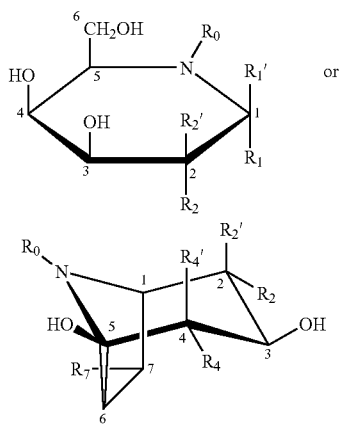

wherein $R_0$ represents H, methyl or ethyl; $R_1$ and $R_1$ independently represent H, OH, a 1-4 carbon alkyl, alkoxy or hydroxyalkyl group (e.g., $CH_2OH$); $R_2$ and $R_2'$ independently represent H, OH or alkyl group (n=1-8); $R_4$ and $R_4'$ independently represent H, OH, or a compound selected from the group consisting of α-allo-homonojirimycin, α-galacto-homonojirimycin, β-1-C-butyl-deoxygalactonojirimycin, calystegine $A_3$, calystegine $B_2$ and their N-alkyl derivatives will alleviate the symptoms of Fabry disease by increasing the residual enzyme activity in patients suffering from Fabry disease.

Compounds expected to be particularly effective for $G_{M1}$-gangliosidosis in the methods of the invention are galactose derivatives having a nitrogen replacing the oxygen in the ring or a nitrogen at the same position of the anomeric position of a pyranose ring, preferably galactose derivatives such as 4-epi-isofagomine and 1-deoxygalactonojirimycin.

Administration of a pharmaceutically effective amount of a compound of formula

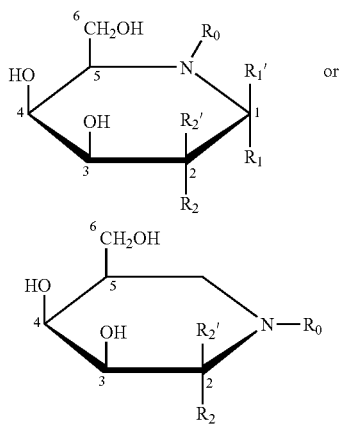

wherein $R_0$ represents H, methyl or ethyl, $R_1$ and $R_1'$ independently represent H. OH, a 1-4 carbon alkyl, alkoxy or hydroxyalkyl group (e.g., $CH_2OH$): $R_2$ and $R_2'$ independently represent H. OH or alkyl group (n=1-8); or a compound selected from the group consisting of 4-epi-isofagomine. and 1-deoxygalactonojirimycin and their N-alkyl derivatives will alleviate the symptoms of $G_{M1}$-gangliosidosis by increasing the residual β-galactosidase activity in patients suffering from $G_{M1}$-gangliosidosis.

Compounds expected to be particularly effective for Gaucher disease in the methods of the invention are glucose derivatives having a nitrogen replacing the oxygen in the ring or a nitrogen at the same position of the anomeric position of a pyranose ring, preferably glucose derivatives such as N-dodecyl-deoxynojirimycin and isofagomine. The term "glucose derivative" is intended to mean that the hydroxyl groups at the C-3 and C-4 positions are equatorial as represented, for example, by the following structures:

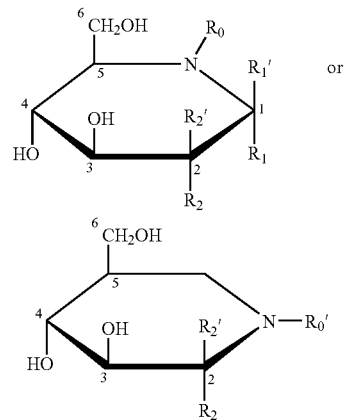

wherein $R_0$ represents H, alkyl chain (n=8-12); $R_0'$ represents H, a straight chain or branched saturated or unsaturated carbon chain containing 1-12 carbon atoms, optionally substituted with a phenyl, hydroxyl or cyclohexyl group; $R_1$ and $R_1'$ independently represent H, OH, a 1-4 carbon alkyl, alkoxy or hydroxyalkyl group (e.g., $CH_2OH$); $R_2$ and $R_2'$ independently represent H, OH or alkyl group (n=1-8).

Other specific competitive inhibitors for β-glucosidase such as for example, calystegine $A_3$, $B_1$, $B_2$ and $C_1$ and their derivatives of these compounds should be useful in the method of the invention. The calystegine compounds can be represented by the formula

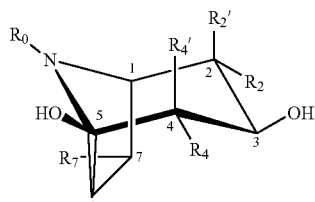

wherein for calystegine $A_3$: $R_0$=H, $R_2$=$R_2'$=H, RA=OH, $R_4'$=$R_7$=H; for calystegine $B_1$: $R_0$=H, $R_2$=$R_2'$=$R_4'$=H, $R_4$=OH, $R_7$=OH; for calystegine $B_2$: $R_0$=H, $R_2$=OH, $R_2'$=$R_4'$=H, $R_1$=OH, $R_7$=H; for calystegine $C_1$: $R_0$=H, $R_2$=OH, $R_2'$=H, $R_4$=OH, $R_4'$=H, $R_7$=OH.

Administration of a pharmaceutically effective amount of a compound of formula

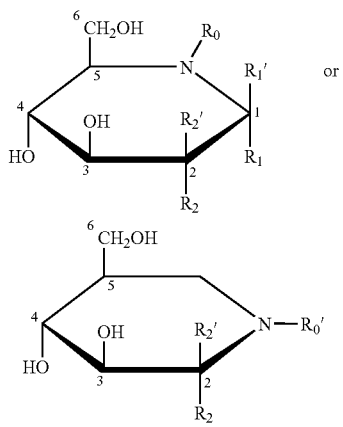

wherein $R_0$ represents H, alkyl chain (n=8-12); $R_0'$ represents H, a straight chain or branched saturated or unsaturated carbon chain containing 1-12 carbon atoms, optionally substituted with a phenyl, hydroxyl or cyclohexyl group; $R_1$ and $R_1'$ independently represent H, OH, a 1-4 carbon alkyl, alkoxy or hydroxyalkyl group (e.g., $CH_2OH$); $R_2$ and $R_2'$ independently represent H, OH or alkyl group (n=1-8): or a compound selected from the group consisting of isofagomine, N-butyl-isofagomine, N-(3-cyclohexylpropyl)-isofagomine, N-(3-phenylpropyl)-isofagomine and N-|(2E,6Z,10Z)-3,7,11-tri-methyldodecatrienyl|-isofagomine. N-dodecyl-deoxynojirimycin will alleviate the symptoms of Gaucher disease by increasing the residual glucocerebrosidase activity in patients suffering from Gaucher disease. Other competitive inhibitors of glucocerebrosidase, such as calystegine compounds and N-alkyl derivatives thereof should also be useful for treating Gaucher disease. Similarly, known competitive inhibitors of other enzymes associated with lysosomal storage disorders listed in Table 1 will be useful in treating those disorders.

Persons of skill in the art will understand that an effective amount of the compounds used in the methods of the invention can be determined by routine experimentation, but is expected to be an amount resulting in serum levels between 0.01 and 100 μM, preferably between 0.01 and 10 μM, most preferably between 0.05 and 1 μM. The effective dose of the compounds is expected to be between 0.5 and 1000 mg/kg body weight/day, preferably between 0.5 and 100 mg/kg body weight/day, most preferably between 1 and 50 mg/kg body weight/day. The compounds can be administered alone or optionally along with pharmaceutically acceptable carriers and excipients, in preformulated dosages. The administration of an effective amount of the compound will result in an increase in the lysosomal enzymatic activity of the cells of a patient sufficient to improve the symptoms of the disease.

In many lysosomal storage diseases, much of the clinical variability and age of onset can be attributed to small differences in the residual activity of the affected enzyme (25a). Pseudodeficiency of lysosomal storage disorders identified as clinically healthy probands with severely reduced activity (10-20% of normal) of a lysosomal enzyme suggests that a small increase of residual enzyme activity could have a large effect on the disease (25b). Particularly in Fabry disease, a small augmentation in enzyme stability resulting in an increase of residual α-Gal A activity is expected to have a significant impact on the disease, based on the observations on the cardiac variants with 10% residual activity (2). Therefore, a small percentage increase of the residual enzyme activity may alleviate symptoms of the disease or significant delay the development of the disease.

Compounds disclosed herein and other competitive inhibitors of enzymes associated with lysosomal storage diseases which will be known to those of skill in the art will be useful according to the invention in methods of enhancing the intracellular activity of normal and mutant enzymes associated with such disorders and treating the disorders.

The numbering of carbons for compounds 2-6, 11-16, 30-32 is the same as in compound 1; the numbering of carbons for compounds 8-10 is the same as in compound 7; the numbering of carbons for compounds 18-20, 22-26 is the same as in compound 17; the numbering of carbons for compounds 33-37 is the same as in compound 21.

FIG. 2. Stereostructure of α-allo-HNJ (9).

A and B are identical, but viewed from different angles. C is a proposed stereo-structure for α-allo-HNJ (9) deduced from NMR analysis. D is a presumed reaction intermediate for α-galactosidase.

Figure 3:
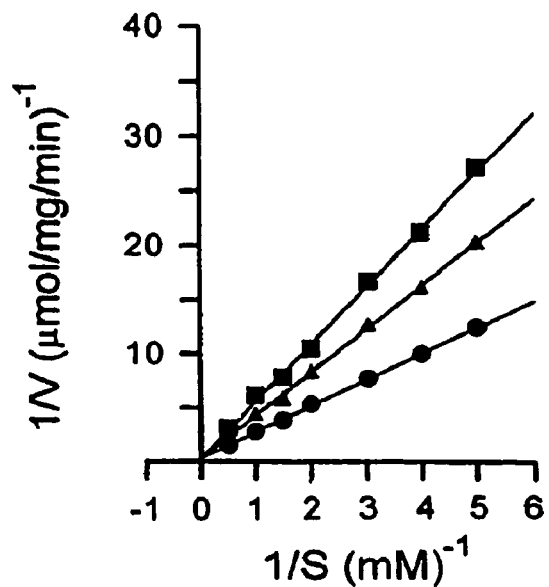
Figure 3:
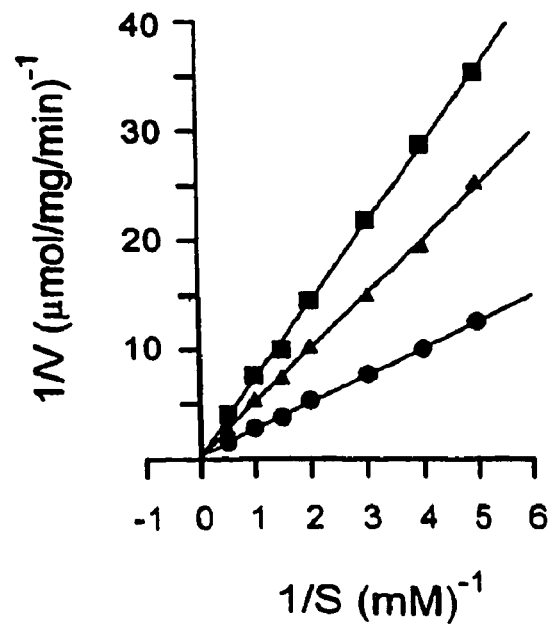
Figure 3:
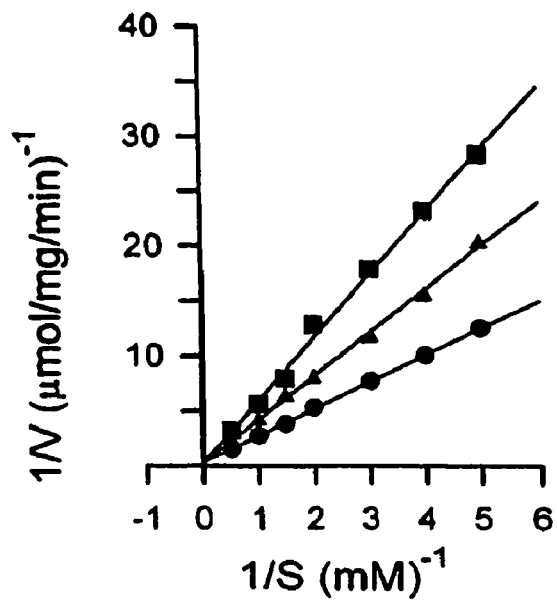
Figure 3:
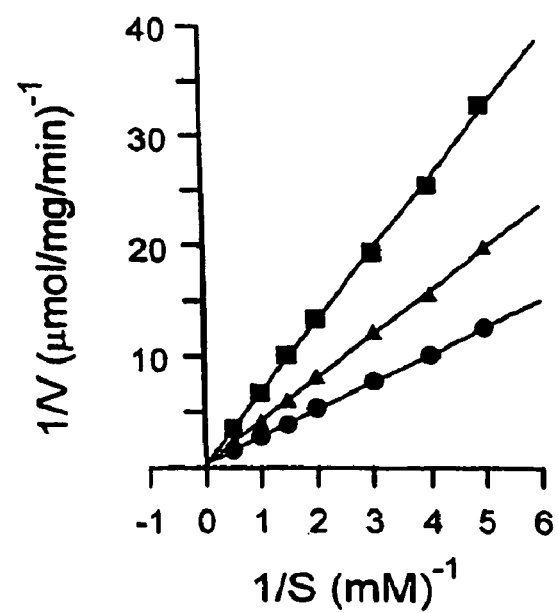

FIG. 3. Lineweaver-Burk plots of DGJ (4) (A), α-allo-HNJ (9) (B), α-galacto-HNJ (10) (C), and β-1-C-butyl-DGJ (16) (D) inhibition of α-Gal A.

The increasing concentrations of substrate were used to determine the $K_m$ and $K_i$ values and the data were plotted as 1/v vs. 1/S. The calculated $K_m$ for p-nitrophenyl-α-D-galactopyranoside was 0.17 mM. (A) Concentrations of 4 were 0 (●), 0.1 μM (▲), and 0.25 μM (■). The calculated $K_i$ value was 0.04 μM. (B) Concentrations of 9 were 0 (●), 2.5 μM (▲), and 5 μM (■). The calculated $K_i$ value was 2.6 μM. (C) Concentrations of 10 were 0 (●), 0.1 μM (▲), and 0.25 μM (■). The calculated $K_i$ value was 0.17 μM. (D) Concentrations of 16 were 0 (●), 10 μM (▲), and 25 μM (■). The calculated $K_i$ value was 16 μM.

FIG. 4. In vitro inhibition (A) and intracellular enhancement (B) of α-Gal A by inhibitors.

(A) Concentrations for 50% inhibition of α-Gal A ($IC_{50}$) were determined with p-nitrophenyl-α-D-galactopyranoside as the substrate. (B) Each inhibitor was added to the culture medium of R301Q lymphoblasts at a concentration of 100 μM. Cells were subsequently incubated for 4 days. After being washed twice with phosphate-buffered saline, the intracellular enzyme activity was determined with 4-MU-α-Gal as the substrate.

Figure 5:
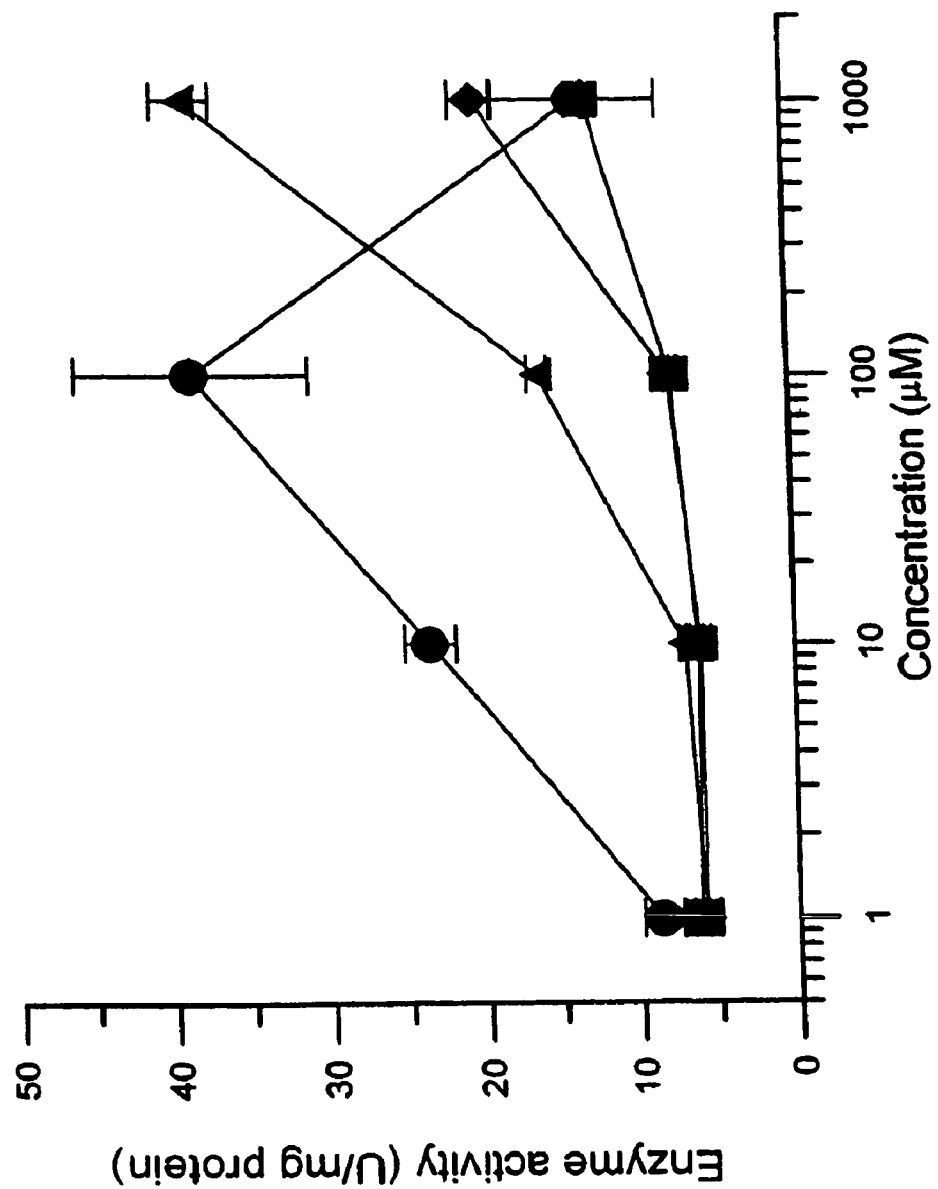

FIG. 5. Effect of the increasing concentrations of selected inhibitors on α-Gal A activity.

R301Q lymphoblasts were cultured with DGJ (4) (●), α-allo-HNJ (9) (■), α-galacto-HNJ (10) (▲), or β-1-C-butyl-DGJ (16) (♦) at 1-1000 μM for 4 days before being collected for enzyme assay.

Figure 6:
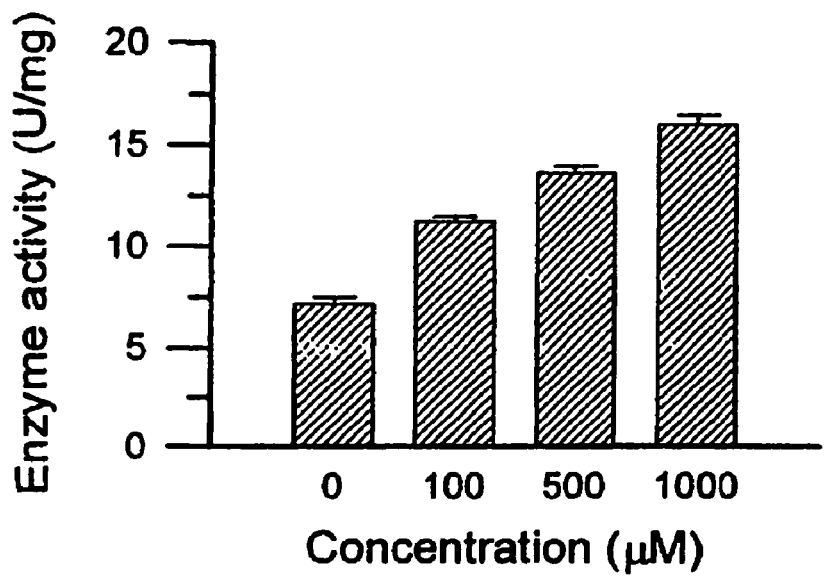
Figure 6:
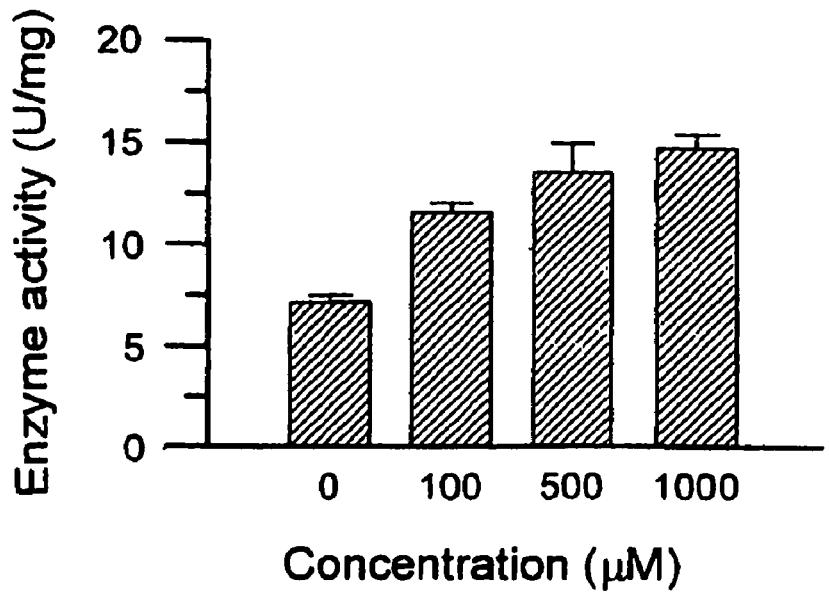
Figure 6:
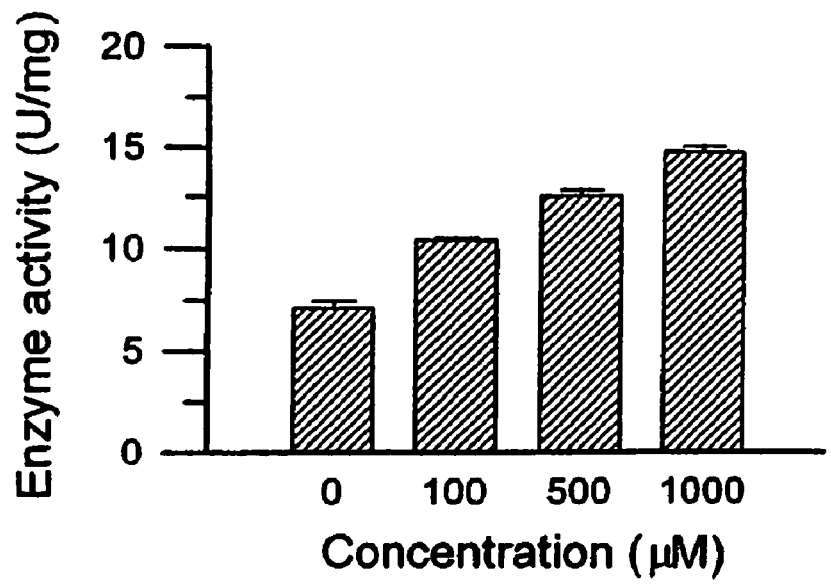
Figure 6:
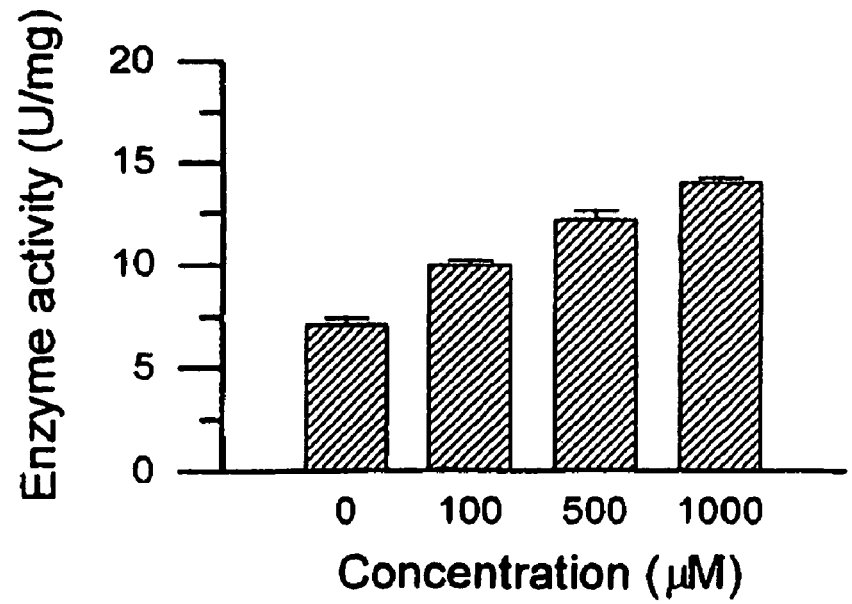

FIG. 6. Intracellular enhancement of α-Gal A activity in Fabry lymphoblasts by calystegine compounds.

R301Q lymphoblasts were cultured with calystegine $A_3$ (17) (A), calystegine $B_2$ (18) (B), N-methyl calystegine $A_3$ (19) (C), or N-methyl calystegine $B_2$ (20) (D) at 100-1000 μM for 4 days before being collected for enzyme assay.

Figure 7:
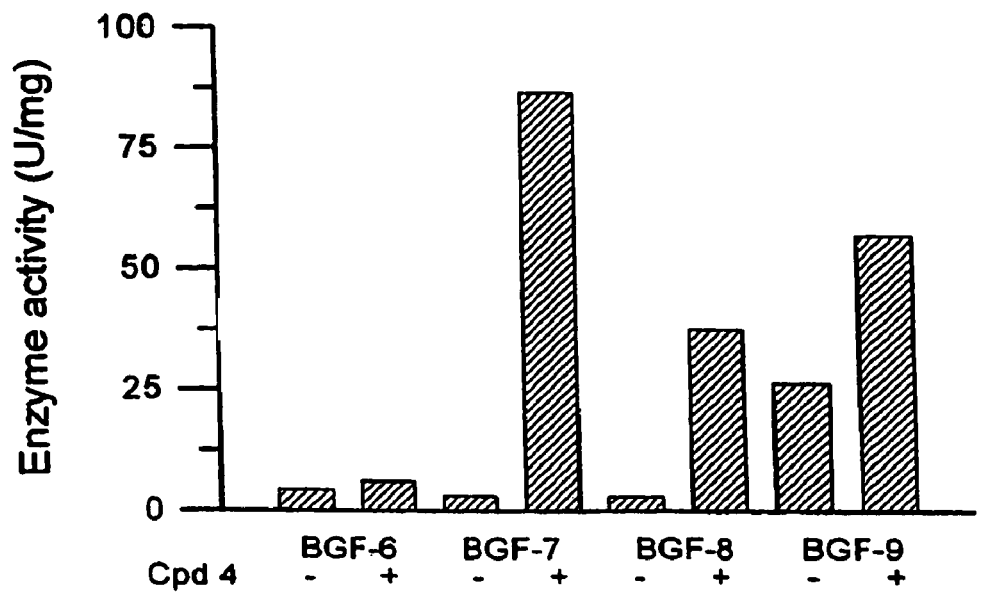
Figure 7:
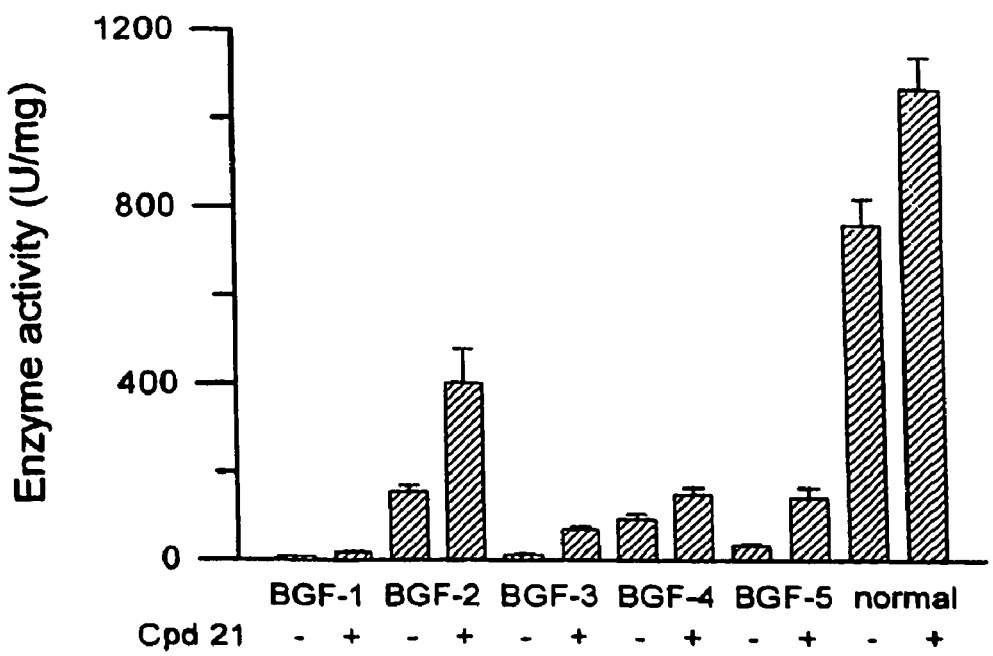

FIG. 7. Intracellular enhancement of β-Gal activity in $G_{M1}$-gangliosidosis fibroblasts.

A, $G_{M1}$-gangliosidosis fibroblasts were cultured with DGJ (4) at 500 μM for 5 days before being collected for enzyme assay. B, $G_{M1}$-gangliosidosis fibroblasts were cultured with 4-epi-isofagomine (21) at 50 μM for 5 days before being collected for enzyme assay. Strains BGF-1 and BGF-6 were diagnosed as infantile type, and all others were juvenile or adult types.

Figure 8:
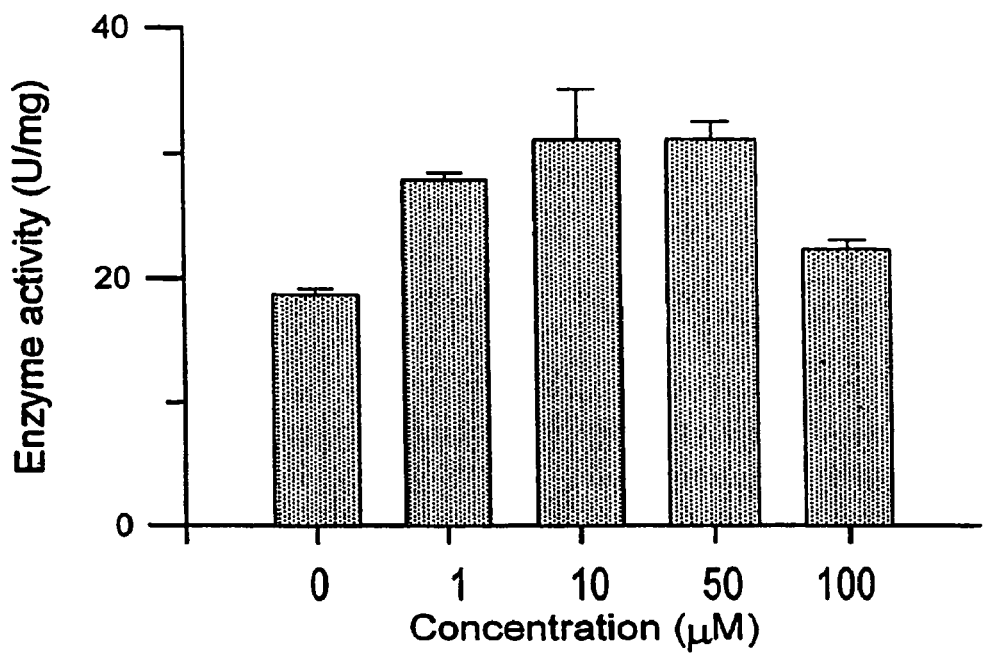
Figure 8:
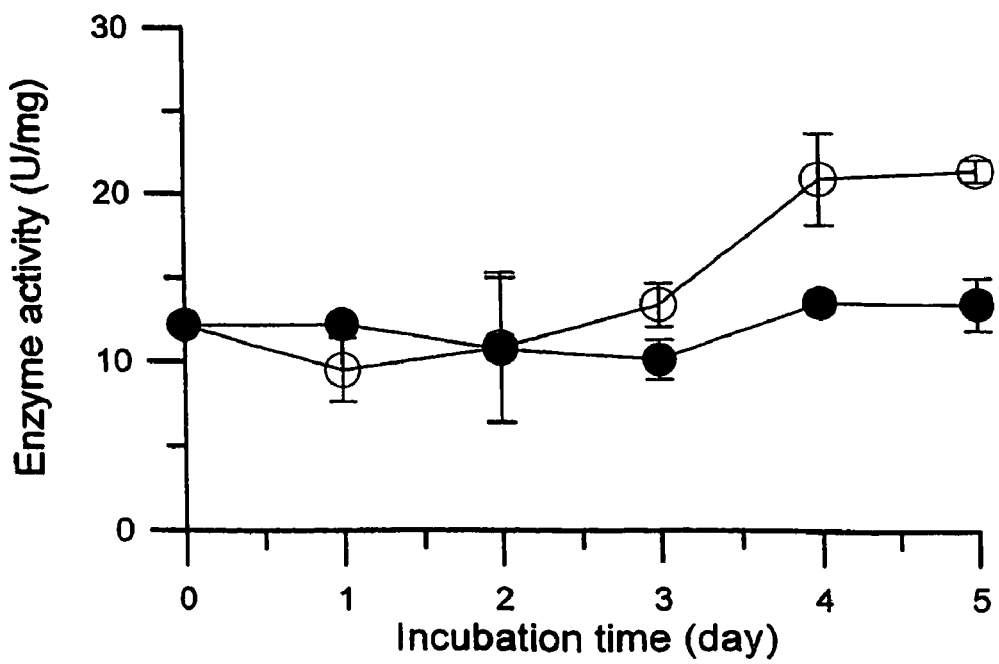

FIG. 8. Intracellular enhancement of β-Glu activity in Gaucher fibroblasts by isofagomine (33).

A, Gaucher fibroblasts (N370S/N370S) were cultured with isofagomine (33) at 1-100 μM for 5 days before being collected for enzyme assay. B, Time course of intracellular enhancement of β-Glu activity in Gaucher cells by isofagomine.

Figure 9:
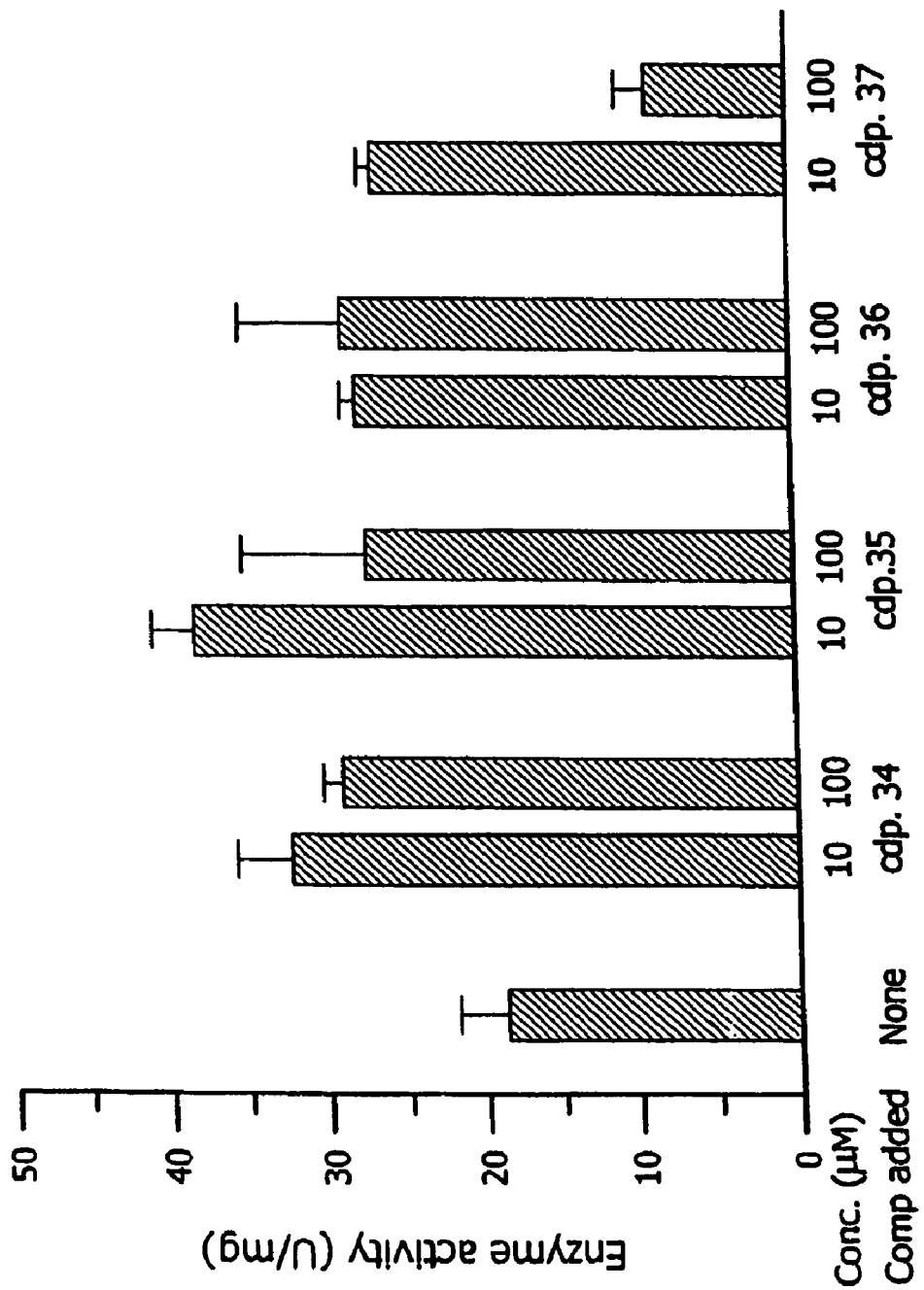

FIG. 9. Intracellular enhancement of β-Glu activity in Gaucher fibroblasts by isofagomine derivatives. Gaucher fibroblasts (N370S/N370S) were cultured with isofagomine derivatives (34-37) at 10 or 100 μM for 5 days before being collected for enzyme assay.

Figure 10:
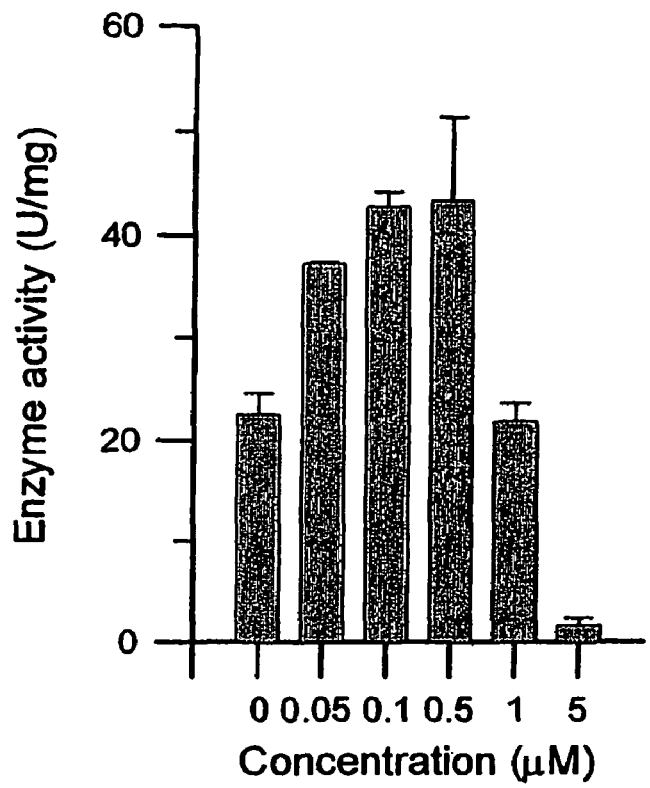
Figure 10:
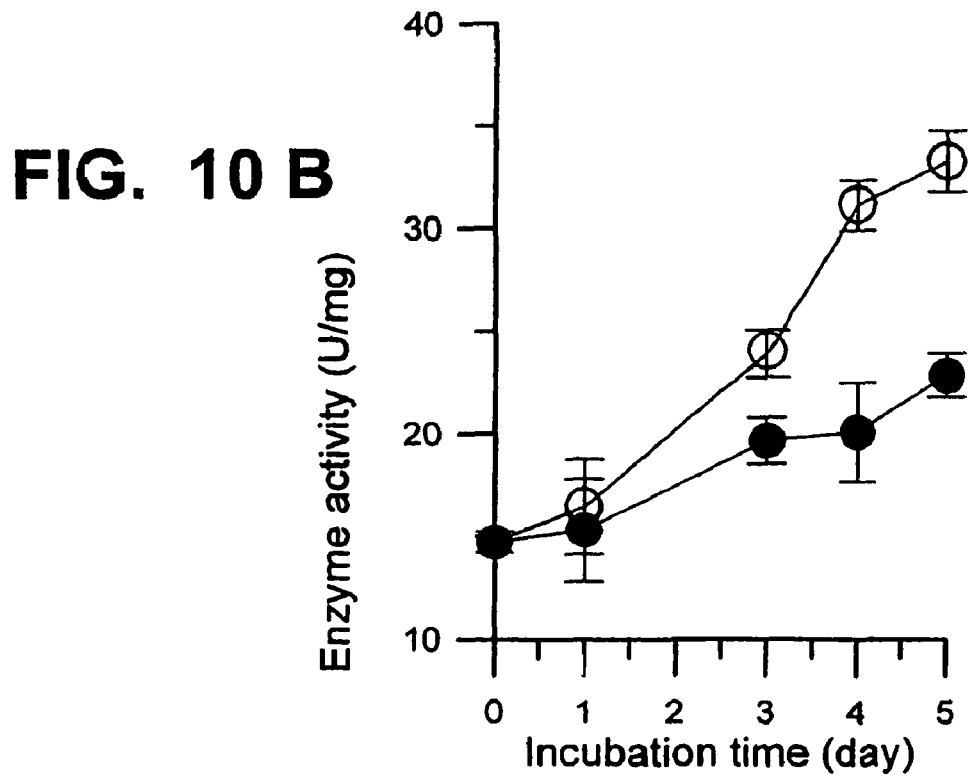

FIG. 10. Intracellular enhancement of β-Glu activity in Gaucher fibroblasts by dodecyl-DNJ (31).

A, Gaucher fibroblasts (N370S/N370S) were cultured with dodecyl-DNJ (31) at 0.05-5 μM for 5 days before being collected for enzyme assay. B, Time course of intracellular enhancement of β-Glu activity in Gaucher cells cultured in the presence (○) or absence (●) of dodecyl-DNJ.

Figure 11:
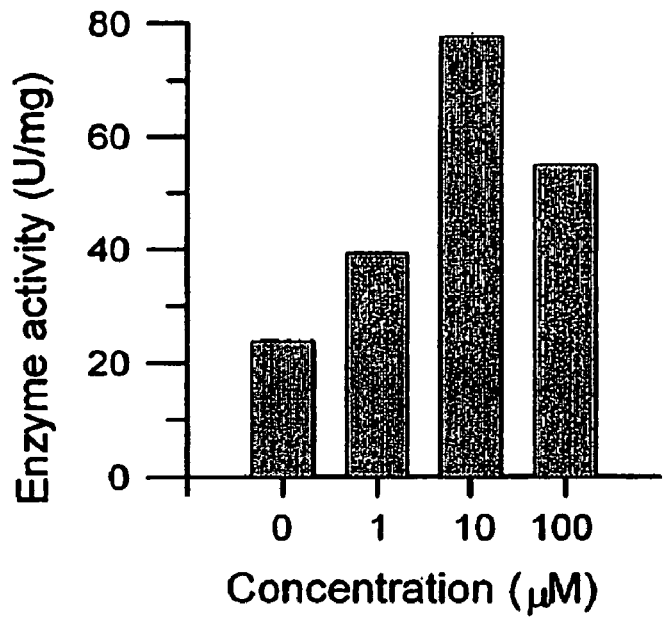
Figure 11:
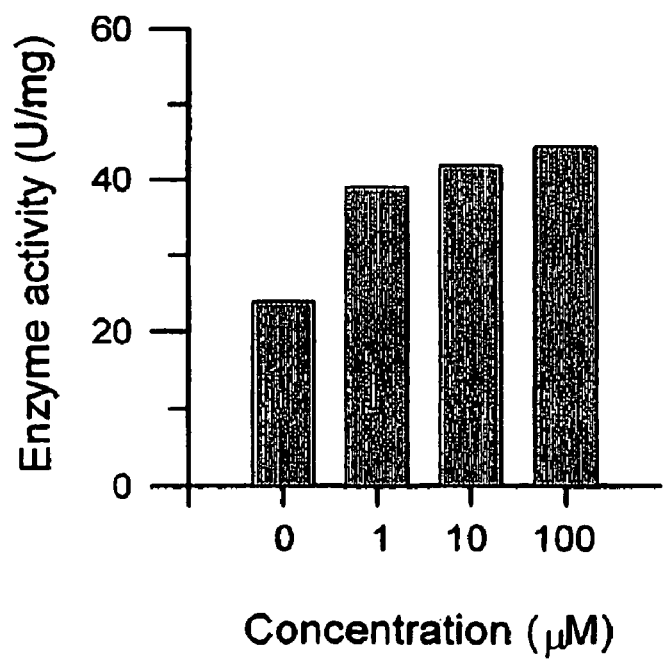
Figure 11:
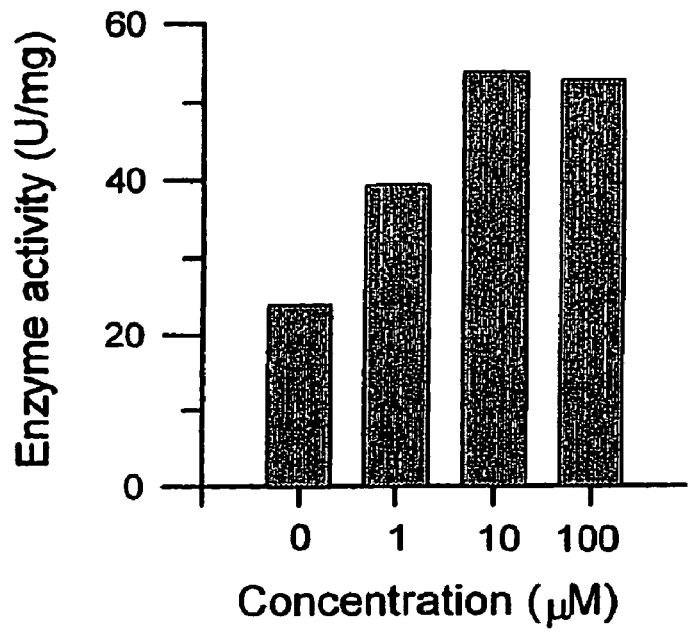
Figure 11:
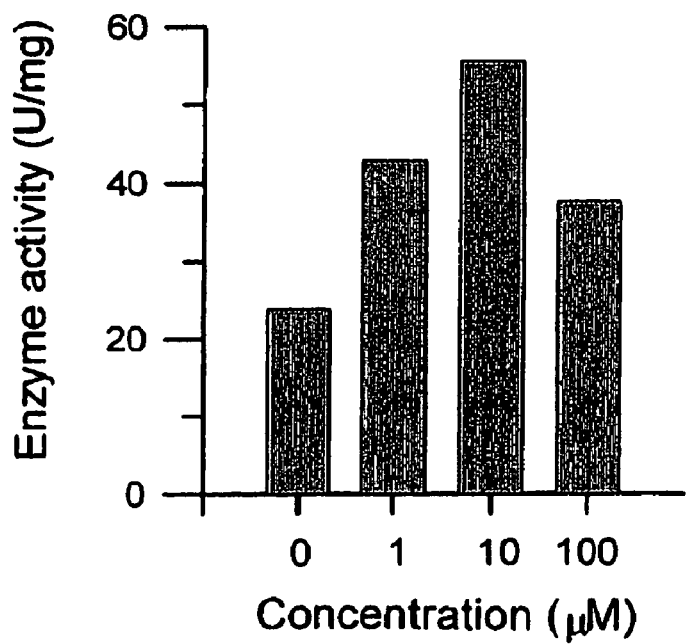

FIG. 11. Intracellular enhancement of β-Glu activity in Gaucher fibroblasts by calystegine compounds. Gaucher fibroblasts (L444P/L444P) were cultured with calystegine compounds (17, 18, 23 and 26) at 1-100 μM for 5 days before being collected for enzyme assay. A, calystegine $B_2$ (18); B, calystegine $B_1$ (23); C, calystegine $A_3$ (17); and D, calystegine $C_1$ (26).

FIG. 12. Structure of iminosugars

DETAILED DESCRIPTION OF THE INVENTION

In the work leading to the present application, the inventors tested a series of naturally occurring and chemically synthesized novel inhibitors for both in vitro inhibition of normal α-Gal A and intracellular enhancement of a mutant α-Gal A activity with Fabry lymphoblasts to demonstrate that potent competitive reversible inhibitors of α-Gal A are effective "chemical chaperones" which can stabilize the mutant enzyme and rescue it from degradation. Applicants now have tested the chemical chaperone strategy with Gaucher disease and $G_{M1}$-gangliosidosis, both of which belong to the lysosomal storage disorder family (26-27), to demonstrate that this therapeutic strategy of using potent competitive inhibitors as chemical chaperones to enhance the residual enzyme activity in the patient's cells is not limited to Fabry disease, and can be applied to Gaucher disease and $G_{M1}$-gangliosidosis as examples of the principle which can be extended to to other lysosomal storage disorders as listed in Table 1.

Materials and Methods

Figure 1:
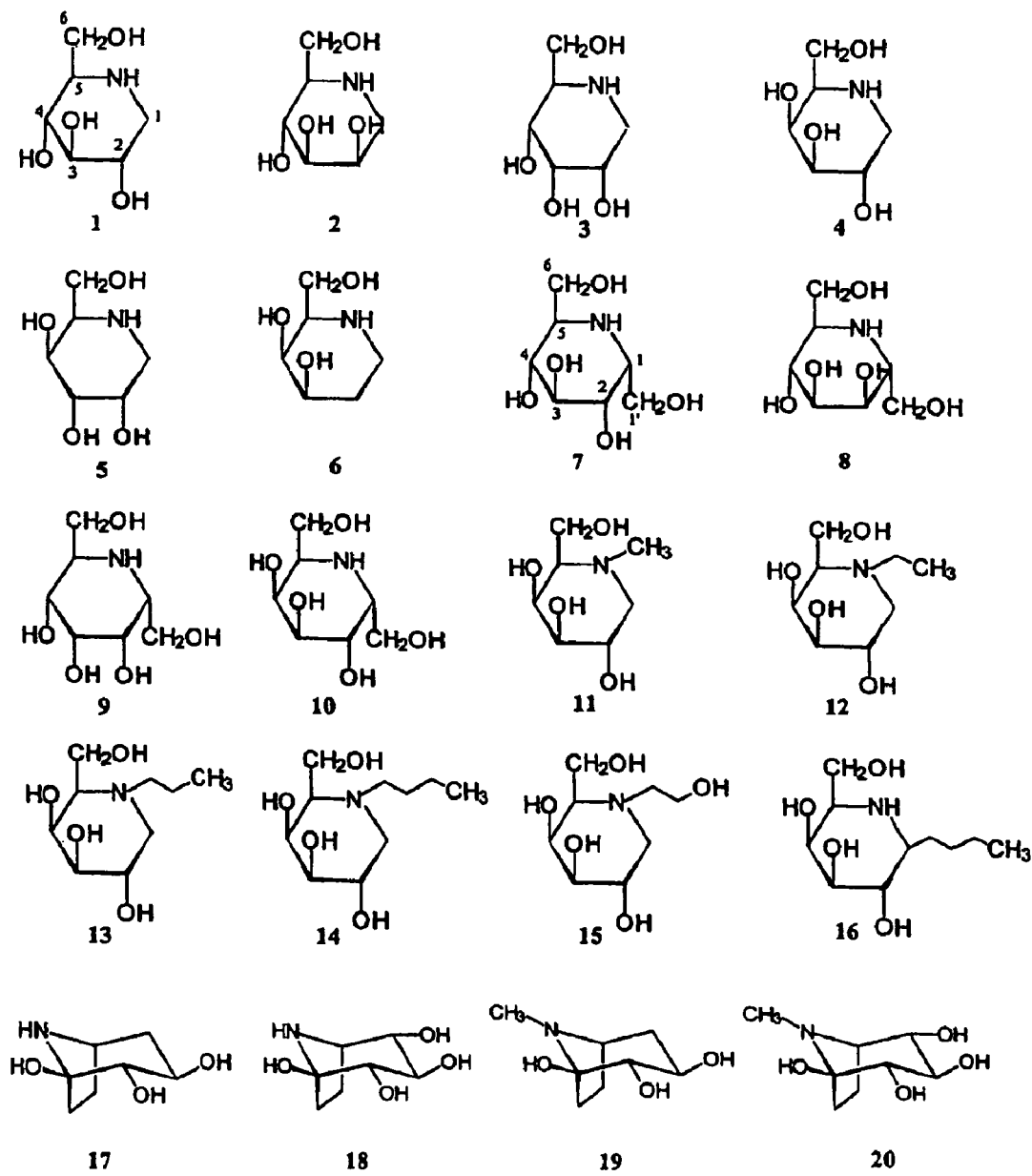
FIG. 1. Structures of inhibitors used in this study.
Figure 1:
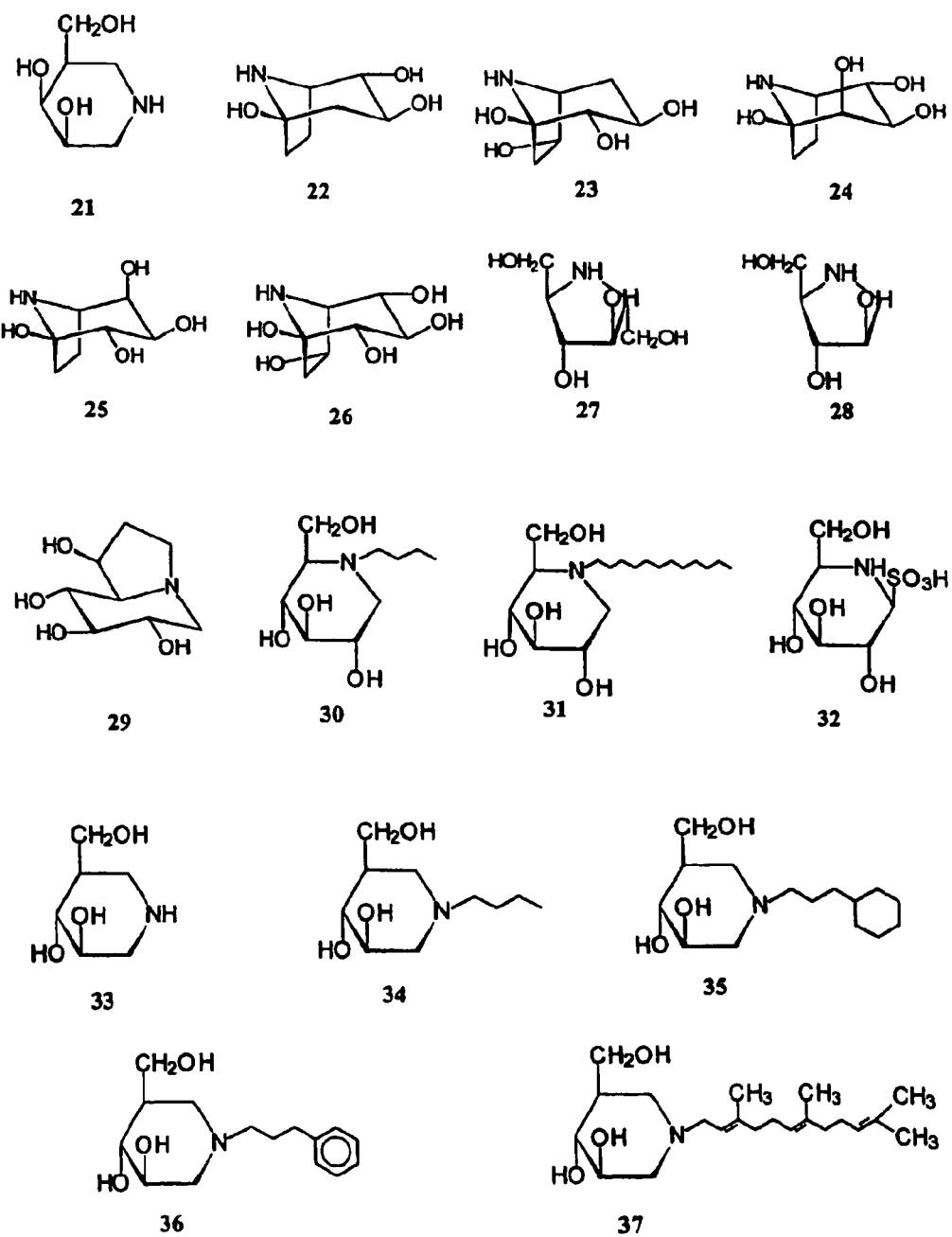

Inhibitors The structures of the Inhibitors used in this Invention are Shown in FIG. 1.

1-deoxynojirimycin (DNJ) (1) was isolated from the roots of *Morus alba* (Moraceae) as described previously (28). 1-Deoxymannojirimycin (manno-DNJ) (2) and 1-deoxy-3,4-diepi-nojirimycin (gulo-DNJ) (5) have been recently isolated from the barks of *Angylocalyx pynaertii* (Leguminosae). 1-Deoxy-3-epi-nojirimycin (allo-DNJ) (3) was prepared by the microbial redox reaction at C-3 of the N-benzyloxycarbonyl derivative of DNJ as described previously (29). 1-Deoxygalactonojirimycin (DGJ) (4) and 1,2-dideoxy-galactonojirimycin (6) were prepared by the chemical epimerization of the 4-OH group of 1 and fagomine, respectively, according to the literature procedure (30). α-Homonojirimycin (α-HNJ) (7), α-homomannojirimycin (α-manno-HNJ) (8), and α-homoallonojirimycin (α-allo-HNJ) (9) were isolated from the whole plant of *Aglaonema treubii* (Araceae) as reported previously (31). α-Homogalactonojirimycin (α-galacto-HNJ) (10) was prepared from 2,3,4,6-tetra-O-benzyl-D-galactose by way of a Wittig chain extension and a mercuricyclization according to the literature procedure (33). N-Methyl-DGJ (11) was prepared by treatment of 4 with 37% HCHO and 80% formic acid according to the reference (34), and the N-ethyl (12), N-propyl (13), N-butyl (14) and N-hydroxyethyl (15) derivatives of 4 were prepared by treatment with the appropriate alkyl bromide and triethylamine in DMF. The reaction mixture of N-alkylation was evaporated in vacuo, and the residual syrup was resolved in MeOH and applied to an Amberlyst 15 column ($H^+$ form), washed with MeOH, eluted with 0.5 M $NH_4OH$, and concentrated. N-Alkylated derivatives were finally purified by Dowex 1X2 ($OH^-$ form) and Amberlite CG-50 ($NH_4^+$ form) chromatography with water as eluent. β-1-C-Butyl-DGJ (16) was isolated from Adenophorae Radix as described previously (35). 4-epi-isofagomine (21), isofagomine (33) and its derivatives (34-37) were chemically synthesized as described previously (40). 2,5-Dideoxy-2,5-imino-D-mannitol (DMDP, 27), 1,4-dideoxy-1,4-imino-D-arabinitol (DAB, 28) were purified from *Derris malaccensis* and *Morus alba*, respectively (29). N-butyl-DNJ (30), N-dodecyl-DNJ (31), castanospermine (29) were from commercial sources. Calystegine $A_3$ (17), calystegine $A_5$ (22), calystegine $B_1$ (23), calystegine $B_2$ (18), calystegine $B_3$ (24), calystegine $B_4$ (25), and calystegine $C_1$ (26) were prepared as published method (36, 40a), N-methyl calystegine $A_3$ (19) and N-methyl calystegine $B_2$ (20) were chemically synthesized.

Structural characterization of some inhibitors The structural characterization of the inhibitors is determined by mass spectrometry and $^{13}C$-NMR, and some of the results are presented below.

1-Deoxynojirimycin (DNJ) (1) HRFABMS m/z 164.0923 $[M+H]^+$ ($C_6H_{14}NO_4$ requires 164.0923). $^{13}C$-NMR (100 MHz, $D_2O$) δ(ppm downfield from internal sodium 3 -(trimethylsilyl)propionate) 51.5 (C-1), 63.3 (C-5), 64.2 (C-6), 73.7 (C-2), 74.3 (C-4), 81.2 (C-3).

1-Deoxymannojirimycin (manno-DNJ) (2) HRFABMS m/z 164.0923 $[M+H]^+$ ($C_6H_{14}NO_4$ requires 164.0923). $^{13}C$-NMR(100 MHz, $D_2O$) δ51.5 (C-1), 63.4 (C-5), 63.7 (C-6), 71.3 (C-4), 72.1 (C-2), 77.5 (C-3).

1-Deoxy-3-epi-nojirimycin (allo-DNJ) (3) HRFABMS m/z 164.0922 $[M+H]^+$ ($C_6H_{14}NO_4$ requires 164.0923). $^{13}C$-NMR (100 MHz, $D_2O$) δ46.9 (C-1), 59.2 (C-5), 60.7 (C-6), 72.7(C-2), 73.3 (C-4), 75.0 (C-3).

1-Deoxygalactonojirimycin (DGJ) (4) HRFABMS m/z 164.0921 $[M+H]^+$ ($C_6H_{14}NO_4$ requires 164.0923). $^{13}C$-NMR(100 MHz, $D_2O$) δ51.9 (C-1), 61.7 (C-5), 64.2 (C-6), 70.9 (C-2), 72.1 (C-4), 77.9 (C-3).

1-Deoxy-3,4-diepi-nojirimycin (gulo-DNJ) (5) HRFABMS m/z 164.0921 [M +H]$^+$ ($C_6H_{14}NO_4$ requires 164.0923). $^{13}C$-NMR (100 MHz, $D_2O$) δ46.9 (C-1), 56.9 (C-5), 63.8 (C-6), 68.3 (C-2), 72.0 (C4),73.0 (C-3).

1,2-Dideoxygalactonojirimycin (6) HRFABMS m/z 148.0972 $[M+H]^+$ ($C_6H_{14}NO3$ requires 148.0974). $^{13}C$-NMR(100 MHz, $D_2O$) δ30.2 (C-2), 45.6 (C-1), 61.8 (C-5), 64.5 (C-6), 70.5 (C-4), 72.7 (C-3).

α-Homonojirimycin (α-HNJ) (7) HRFABMS m/z 194.1025 $[M+H]^+$ ($C_7H_{16}NO_5$ requires 194.1028). $^{13}C$-NMR (100 MHz, $D_2O$) ,δ56.9 (C-5), 59.1 (C-1'), 59.7 (C-1), 64.8 (C-6), 74.4 (C-2), 74.9 (C-4), 77.1 (C-3).

α-Homomannojirimycin (α-manno-HNJ) (8) HRFABMS m/z 194.1026 [M+]$^+$ ($C_7H_{16}NO_5$ requires 194.1028). $^{13}C$-

NMR (100 MHz, D$_2$O) δ58.6 (C-5), 61.4 (C-1), 62.2 (C-1'), 63.9 (C-6), 71.4 (C-4), 71.6 (C-2), 74.7 (C-3).

α-Homoallonojirimycin (α-allo-HNJ) (9) HRFABMS m/z 194.1024 [M+H]$^+$ (C$_7$H$_{16}$NO$_5$ requires 194.1028). $^{13}$C-NMR (100 MHz, D$_2$O) δ57.2 (C-5), 58.1 (C-1), 62.7 (C-1'), 63.5 (C-6), 72.0 (C-4), 72.1 (C-3), 72.2 (C-2).

α-Homogalactonojirimycin (α-galacto-HNJ) (10) HRFABMS m/z 194.1028 [M+H]$^+$ (C$_7$H$_{16}$NO$_5$ requires 194.1028). $^{13}$C-NMR(100 MHz, D$_2$O), δ55.8 (C-5), 59.3 (C-1), 59.6 (C-1'), 64.5 (C-6), 71.8 (C-2), 71.9 (C-4), 73.8 (C-3).

N-Methyl-1-deoxygalactonojirimycin (N-Me-DGJ) (11) HRFABMS m/z 178.1081 [M+H]$^+$ (C$_7$H$_{16}$NO$_4$ requires 178.1079). $^{13}$C-NMR (100 MHz, D$_2$O) δ44.2 (N—CH$_3$), 62.9 (C-1), 63.6 (C-6), 68.5 (C-2), 69.7 (C-5), 73.0 (C-4), 77.8 (C-3).

N-Ethyl-1-deoxygalactonojirimycin (N-Et-DGJ) (12) HRFABMS m/z 192.1237 [M+H]$^+$ (C8H$_{18}$NO$_4$ requires 192.1236). $^{13}$C-NMR (100 MHz, D$_2$O) δ10.7, 48.9 (N-ethyl), 57.8 (C-1), 63.2 (C-6), 65.0 (C-5), 69.9 (C-2), 73.0 (C4), 77.9 (C-3).

N-Propyl-1-deoxygalactonojirimycin (N-Pr-DGJ) (13) HRFABMS m/z 206.1392 [M+H]$^+$ (C9H$_{20}$NO$_4$ requires 206.1392). $^{13}$C-NMR (100 MHz, D$_2$O) δ13.9, 19.2, 57.2 (N-propyl), 58.6 (C-1), 63.3 (C-6), 65.5 (C-5), 69.9 (C-2), 73.0 (C4), 77.9 (C-3).

N-Butyl-1-deoxygalactonojirimycin (N-Bu-DGJ) (14) HRFABMS m/z 220.1546 [M+H]$^+$ (C$_{10}$H22NO$_4$ requires 220.1549). $^{13}$C-NMR (100 MHz, D$_2$O) δ16.1, 23.0, 27.9, 55.0 (N-butyl), 58.6 (C-1), 63.3 (C-6), 65.5 (C-5), 69.9 (C-2), 73.0 (C-4), 77.9 (C-3).

N-Hydroxyethyl-l-deoxygalactonojirimycin (N-HE-DGJ) (15) HRFABMS m/z 208.1183 [M +H]$^+$ (C$_8$H$_{18}$NO$_5$ requires 208.1185). $^{13}$C-NMR (100 MHz, D$_2$O) δ56.0 (N-CH$_2$—), 59.2 (C-1), 60.9 (N—CH$_2$CH$_2$OH), 63.7 (C-6), 66.4 (C-5), 69.7 (C-2), 73.3 (C-4), 77.8 (C-3).

β-1-C-Butyl-deoxygalactonojirimycin (16) HRFABMS m/z 220.1543 [M+]$^+$ (C$_{10}$H$_{22}$NO$_4$ requires 220.1549). $^{13}$C-NMR(100 MHz, D$_2$O) (δ16.1, 25.0, 29.6, 33.5 (C-butyl), 61.1 (C-5), 61.8 (C-1), 64.2 (C-6), 71.8 (C-4), 74.9 (C-2), 77.9 (C-3).

Enzyme and in vitro enzyme assay α-Gal A was expressed from Sf-9 insect cells infected with a recombinant baculovirus encoding normal α-Gal A gene and purified to homogeneity by concanavalin A-Sepharose and Mono Q (Pharmacia LKB Biotechnology, Uppsala, Sweden) column chromatography according to the published methods (37). The enzyme activity was assayed with 2 mM p-nitrophenyl-α-D-galactoside as substrate in the presence of bovine serum albumin (3 mg/ml) at pH 4.5.

Cell culture The Epstein-Barr virus-transformed lymphoblast lines from a normal adult and a Fabry patient with R301Q mutation in α-Gal A (38) were cultured in RPMI-1640 medium (Nissui Pharmaceutical Co., Tokyo, Japan) supplemented with 10% fetal calf serum (FCS) at 37° C. under 5% CO$_2$. Human fibroblasts from Gaucher and G$_{M1}$-gangliosidosis patients were cultured in McCoy 5A medium supplemented with 10% FCS at 37° C. under 5% CO$_2$.

Intracellular α-Gal A assay Cells were cultured in the presence or absence of inhibitor for 4 days. After being washed twice with phosphate-buffered -saline (PBS), the cells were harvested and homogenized in 200 μl of H$_2$O, and 10 μl of the supernatant obtained by centrifugation at 10,000 g was incubated at 37° C. with 50 μl of the substrate solution composed by 6 mM 4-methylumbelliferyl α-D-galactoside (4-MU-α-Gal) and 90 mM N-acetylgalactosamine in 0.1 M citrate buffer (pH 4.5) for enzyme assay. One unit of intracellular enzyme activity was defined as one nmol of 4-methylumbelliferone released per hour at 37° C.

Intracellular galactosidase assay Cells were cultured in the presence or absence of inhibitor for 5 days. After being washed twice with PBS, the cells were harvested and homogenized in 200 μl of H$_2$O, and 10 μl of the supernatant obtained by centrifugation at 10,000 g was incubated at 37° C. with 50 μl of the substrate solution of 1 mM 4-methylumbelliferyl β-D-galactoside (4-MU-β-Gal) in 0.1 M citrate buffer (pH 4.5) for enzyme assay. One unit of intracellular enzyme activity was defined as one nmol of 4-methylumbelliferone released per hour at 37° C.

Intracellular glucocerebrosidase assay Cells were cultured in the presence or absence of inhibitor for 5 days. After being washed twice with PBS, the cells were harvested and homogenized in 200 μl of buffer I composed by 0.25% sodium taurocholate, 0. 1% Triton X-100 and 0.1 M citrate buffer (pH 5.2). The supernatant (10 μl) obtained by centrifugation at 10,000 g was incubated at 37° C. with 50 μl of the substrate solution of 3 mM 4-methylumbelliferyl β-D-glucoside (4-MU-β-Glu) in the buffer I for determination of total β-glucosidase activity. The neutral β-glucosidase activity was determined by performing the same assay except pre-incubation of the enzyme solution with 3 mM conduritol B epoxide (an irreversible inhibitor of acid β-Glu) at room temperature for 30 min. The glucocerebrosidase activity was determined by subtracting the neutral β-glucosidase activity from the total enzyme activity. One unit of intracellular enzyme activity was defined as one nmol of 4-methylumbelliferone released per hour at 37° C.

EXAMPLE 1

In vitro Inhibition and Intracellular Enhancement of α-Gal A in Fabry Lymphoblasts Structural Basis of In Vitro Inhibition of α-Gal A The summary of IC$_{50}$ and selected K$_i$ values of DGJ and its derivatives are shown in Table 2.

TABLE 2

In vitro inhibition of α-Gal A by DGJ derivatives.

| Inhibitor | IC$_{50}$ and (K$_i$)$^a$ |
|---|---|
| 1-deoxynojirimycin (DNJ) (1) | 830 |
| manno-DNJ (2) | N.I.$^b$ |
| allo-DNJ (3) | N.I. |
| galacto-DNJ (DGJ) (4) | 0.04 (K$_i$, 0.04) |
| gulo-DNJ (5) | N.I. |
| 2-deoxy-DGJ (6) | 250 |
| α-homonojirimycin (α-HNJ) (7) | N.I. |
| α-manno-HNJ (8) | 464 |
| α-allo-HNJ (9) | 4.3 (K$_i$, 2.6) |
| α-galacto-HNJ (α-HGJ) (10) | 0.21 (K$_i$, 0.17) |
| N-methyl-DGJ (11) | 96 |
| N-ethyl-DGJ (12) | 306 |
| N-propyl-DGJ (13) | 301 |
| N-butyl-DGJ (14) | 300 |
| N-hydroxyethyl-DGJ (15) | 520 |
| β-1-C-butyl-DGJ (16) | 24 (K$_i$, 16) |

IC$_{50}$ values (i.e. inhibitor concentration giving 50% inhibition) were determined by variation of inhibitor concentrations. K$_i$ values were evaluated from the slope of Lineweaver-Burk plots. Assays were performed as described under "Methods." All constants are expressed in micromolar.
$^a$Km of α-Gal A was determined as 0.17 mM with p-nitrophenyl-α-D-galactopyranoside.
$^b$Inhibition was less than 50% at 1000 μM.

DGJ and its Isomers

DGJ (galacto-DNJ) was synthesized from D-glucose and found to be an extremely powerful inhibitor of coffee bean α-galactosidase (39). In the development of the present invention, both $IC_{50}$ and $K_i$ values of DGJ toward human lysosomal α-Gal A were calculated to be 0.04 μM (Table 2, FIG. 3A). DNJ (1) was a weak inhibitor of this enzyme with an $IC_{50}$ value of 830 μM, while other isomers such as manno- (2), allo-(3), and gulo-DNJ (5) showed no appreciable inhibition even at 1000 μM. The deoxygenation at C-2 of DGJ (6) reduced its inhibitory potential over 6000-fold. These results suggested to Applicants that a galactosyl configuration of an imino sugar is preferable for the inhibition of α-Gal A.

α-HNJ and Isomers

α-HNJ (7) was not an inhibitor of α-Gal A, but α-manno-HNJ (8) was a weak inhibitor of the enzyme. α-galacto-HNJ (10) mimicking α-D-galactopyranose was first expected to be a more specific and potent inhibitor of α-Gal A than DGJ. From $^1$H-NMR studies, the $^3J_{H,H}$-coupling constants ($J_{2,3}$=9.8 Hz, $J_{3,4}$=3.0 Hz, $J_{4,5}$=2.6 Hz,) observed for α-galacto-HNJ (10) clearly showed that this compound is predominantly in a chair conformation which maintained the ground-state structure of the substrate. However, insertion of a hydroxymethyl group to the α-anomeric position of DGJ decreased the affinity for α-Gal A by approximately 4-fold. Surprisingly, α-allo-HNJ (9) showed a fairly potent inhibitory activity toward α-Gal A, with an $IC_{50}$ value of 4.3 μM. From its structure, this compound could form two different conformations as shown in FIG. 2, α-allo-HNJ (FIG. 2A) vs. C-2 epimer of α-galacto-HNJ (FIG. 2B). The $J_{H,H}$-coupling constants in compound 9 ($J_{1,2}$=4.6 Hz; $J_{2,3}$=2.9 Hz; $J_{3,4}$=2.9 Hz; $J_{4,5}$=6.5 Hz) indicated that the conformation deviates from a chair form as a result of the 1,3 syn-diaxial interaction between the substituents at C-2 and C-4 (FIG. 2B). Furthermore, the C-5 carbon in the $^{13}$C-NMR spectrum of 9 is observed as a broad signal, presumably due to "wobble" at C-5. The potent inhibitory activity of α-allo-HNJ (9) toward α-Gal A may be due to the partial stereochemical and conformational similarities between a flexible α-allo-HNJ conformation (FIG. 2C) and a galactosyl cation (FIG. 2D), which has been presumed to be a transition state intermediate in the enzyme-catalyzed galactoside hydrolysis (40).

N-Alkyl Derivatives of DGJ

The N-alkyl derivatives of DGJ were studied for α-Gal A inhibition because N-alkylation of DNJ and α-HNJ resulted in analogues with increased potency and substrate specificity on digestive α-glucosidases and processing α-glucosidase I (41-44), and N-alkylation of DNJ and DGJ increased inhibitory potential toward glucosyltransferase (45, 46). However, N-alkylation of DGJ markedly lowered its inhibitory activity toward α-Gal A (Table 3), suggesting that modification of the imino group is not preferred for inhibition of α-Gal A. The naturally occurring DGJ derivative, β-1-C-butyl-DGJ, has recently been isolated from Adenophorae Radix as a potent inhibitor of coffee bean α-galactosidase with an $IC_{50}$ value of 0.71 μM (35). The $IC_{50}$ value for α-Gal A was determined to be 24 μM.

Inhibition Mode of DGJ and its Derivatives

The inhibition mode of four potent inhibitors of α-Gal A, DGJ (4), α-galacto-HNJ (10), α-allo-HNJ (9) and β-1-C-butyl-DGJ (16) were studied. Lineweaver-Burk plots indicated that they are competitive inhibitors of α-Gal A (FIG. 3). The calculated Ki values of DGJ, α-galacto-HNJ, α-allo-HNJ and β-1-C-butyl-DGJ were found to be 0.04 μM, 0.25 μM, 2.6 μM, and 16 μM, respectively.

Intracellular Enhancement of α-Gal A by the Enzyme Inhibitors

As shown in FIG. 4B, those DGJ derivatives that showed high inhibitory activity toward α-Gal A were tested for enhancement of intracellular α-Gal A activity in R301Q lymphoblasts. Treatment with DGJ at 100 μM for 4 days increased enzyme activity in R301Q lymphoblasts by about 14-fold reaching 49% of normal. Enzyme activity was increased 5.2-fold, 2.4-fold, and 2.3-fold by cultivation with α-galacto-HNJ, α-allo-HNJ, and β-1-C-butyl-DGJ at 100 μM, respectively, while weak inhibitors such as N-alkyl derivatives of DGJ showed only a slight enhancement effect at 100 μM. The effectiveness of intracellular enhancement paralleled to the in vitro inhibitory activity (FIG. 4A), indicating that a potent inhibitor serves as an effective enhancer.

The enzyme activity in R301Q lymphoblasts was elevated with increasing inhibitor concentration in a certain range (for DGJ, 1-100 μM, FIG. 5). α-galacto-HNJ, α-allo-HNJ, and β-1-C-butyl-DGJ enhanced the α-Gal A activity by 12.5-, 3.9-, and 6.3-fold at 1000 μM, respectively. However, higher concentrations significantly reduced the enhancement effect, presumably causing inhibition of the enzyme activity. Applicants confirmed that inclusion of DGJ in the medium at 20 μM did not cause intracellular inhibition of globotriaosylceramide metabolism, indicating that intracellular DGJ concentration appeared to be lower than the concentration normally required to inhibit the intracellular enzyme activity at that condition (24). Intralysosomal enzyme activity may not be inhibited by α-galacto-HNJ, α-allo-HNJ, and β-1-C-butyl-DGJ added in the culture medium at 1000 μM, because these compounds exhibited weaker inhibitory activity than DGJ.

Although β-1-C-butyl-DGJ was a less effective inhibitor of α-Gal A than α-allo-HNJ ($K_i$=16 μM vs $K_i$=2.6 μM), both enhancement effects were the same at 100 μM, and the effect of β-1-C-butyl-DGJ at 1000 μM was higher than that by α-allo-HNJ at the same concentration (FIG. 5). This suggested that the bioavailability of β-1-C-butyl-DGJ may be better than α-allo-HNJ, because increase of lipophilicity resulting from the C-alkylation at C-1 of DGJ may enhance the efficient transport across cell and ER membranes.

Calystegine compounds are polyhydroxylated nortropane alkaloids. Certain of these alkaloids exhibit potent inhibitory activities against glycosidases (47). The enzyme activity in R301Q lymphoblasts was also elevated with increasing concentration of calystegine $A_3$ (FIG. 6A), calystegine $B_2$ (FIG. 6B), N-methyl-calystegine $A_3$ (FIG. 6C), and N-methyl-calystegine $B_2$ (FIG. 6D), respectively in a range of 100-1000 μM.

The above results further supported Applicants' therapeutic concept that potent competitive inhibitors can serve as efficient chemical chaperones to enhance intracellular mutant enzyme activity in cells derived from patients of Fabry disease. According to this theoretical concept, more potent inhibitors serve as more powerful chemical chaperones. As shown in the following examples, this therapeutic strategy of using potent competitive inhibitors or substrate analogs is not limited to Fabry disease, but also applicable to other lysosomal storage disorders and general hereditary disorders resulted from protein folding defects, such as, but not limited to, $\alpha_1$-antitrypsin deficiency, familial hypercholesterolemia, Alzheimer's disease, Marfan syndrome, osteogenesis imperfecta, carbohydrate-deficient glycoprotein syndrome, and Maroteaux-Lamy syndrome.

EXAMPLE 2

Intracellular Enhancement of β-galactosidase Activity in Fibroblasts from $G_{M1}$-gangliosidosis Patients $G_{M1}$-gangliosidosis is a progressive neurological disease caused by hereditary deficiency of lysosomal acid β-galactosidase (β-Gal) which hydrolyses the terminal β-galactosidic residual of ganglioside $G_{M1}$ and other glycoconjugates (27). Three clinical forms are described as infantile type (severe form), juvenile type (sub-severe type), and adult onset type (mild type). No treatment is available for this disorder.

Applicants applied the strategy of using potent inhibitors as chemical chaperones to enhance intracellular mutant enzyme activity to human $G_{M1}$-gangliosidosis fibroblasts.

Human $G_{M1}$-gangliosidosis fibroblasts were cultured for 5 days with DGJ (4) and 4-epi-isofagomine (21) (both are inhibitors of β-Gal) at 500 μM, and 50 μM, respectively (FIG. 6). The enhancement effect was not efficient with the fibroblasts from patients of infant type disease (BGF-1 and BGF-6). However, the intracellular enzyme activities in fibroblasts established from patients diagnosed as juvenile and adult types disease were elevated to 9-53% of normal (FIG. 7B). The residual enzyme activity in BGF-7 was markedly increased 27-fold by inclusion of compound 4 at 500 μM (FIG. 7A). These results indicate that compound 4 and 21 are powerful chemical chaperones for β-Gal, and can be used as potential therapeutic agents for treatment of $G_{M1}$-gangliosidosis.

EXAMPLE 3

Intracellular Enhancement of Glucocerebrosidase Activity in Fibroblasts from Gaucher Patients Gaucher disease is characterized by the accumulation of glucosylceramide (glucocerebroside) due to the deficient activity of lysosomal acid β-glucosidase (glucocerebrosidase, β-Glu) (26). Three types of Gaucher disease have been identified: 1) type 1 (adult-onset), lack of primary central nervous system involvement; 2) type 2 (infantile-onset), acute neuronopathic form of the disease with an early onset; type 3 (late-infantile/juvenile-onset), subacute neuronopathic form. Enzyme replacement therapy is effective only for type 1 disease.

In Vitro Inhibition of Glucocerebrosidase

Various natural and synthetic compounds were tested with human normal β-Glu for inhibitory activity, and the $IC_{50}$ values are shown in Table 3.

TABLE 3

In vitro inhibition of human β-glucocerebrosidase.

| Inhibitor | $IC_{50}$ |
|---|---|
| Calystegine $A_3$ (17) | 3.1 |
| Calystegine $A_5$ (22) | 31 |
| Calystegine $B_1$ (23) | 2.5 |
| Calystegine $B_2$ (18) | 0.99 |
| Calystegine $B_3$ (24) | 76 |
| Calystegine $B_4$ (25) | 82 |
| Calystegine $C_1$ (26) | 2.5 |
| N-Metyl-calystegine $B_2$ (20) | 320 |
| DMDP (27) | 280 |
| DAB (28) | 160 |
| Castanospermine (29) | 19 |
| DNJ (1) | 240 |
| N-Butyl-DNJ (30) | 270 |
| N-Dodecyl-DNJ (31) | 0.05 |
| DNJ bisulfite (32) | 28 |
| Isofagomine (33) | 0.04 |
| N-Butyl-isofagomine (34) | 44 |
| N-(3-cyclohexylpropyl)-isofagomine (35) | 100 |
| N-(3-phenylpropyl)-isofagomine (36) | 69 |
| N-[(2E, 6Z, 10Z)-3,7,11-trimethyldodecatrienyl]-isofagomine (37) | 1.5 |

$IC_{50}$ values were determined by variation of inhibitor concentrations. Assays were performed with glucocerebrosidase in 0.1 M citrate buffer (pH 5.2) using 4-MU-β-Glu as substrate. All constants are expressed in micromolar.

Several potent inhibitors were found among calystegine compounds. Calystegine $B_2$ (18) ($IC_{50}$ value, 0.99 μM), calystegine $B_1$ (23) (2.5 μM), calystegine $C_1$ (26) (2.5 μM), and calystegine $A_3$ (17) (3.1 μM) were the best inhibitors in this class. Castanospermine (29) is a known potent inhibitor for α-glucosidase, however, it also present fair inhibitory activity against β-Glu (19 μM). DNJ (1) and N-butyl-DNJ (30) were weak inhibitors for this enzyme, however, N-dodecyl-DNJ (31) turned to be one of the most potent inhibitor with $IC_{50}$ at 0.05 μM. Since DNJ and N-butyl-DNJ were moderate inhibitors of the enzyme, the high potency of this compound (31) is believed from the long alkyl chain in the molecular which is probably recognized by the recognition domain normally recognizing the ceramide part of the substrate. Isofagomine (IFG, 33) was reported as a potent inhibitor against almond β-galactosidase (40), and revealed as the most potent inhibitor among those tested with $IC_{50}$ value at 0.04 μM. Modification of the imino group (compounds 34-37) of IFG reduced inhibitory activity substantially. This result consistent with Applicants' earlier finding with α-Gal A in which alkyl modification of DGJ nullified its inhibitory activity. Noticeably, compound 37 which contains a 12 carbon chain in the backbone increased 30-fold in its potency compared with compound 32 which contains a 4 carbon chain. Combined with the result generated from DNJ (1) and N-dodecyl-DNJ (31), it is expected that N-dodecyl-IFG serves as a powerful inhibitor for human β-Glu. In accordance with the invention, these inhibitors should be effective in enhancing activity of the defective enzyme associated with Gaucher disease and treatment of the disorder.

Intracellular Enhancement of β-Glu Activity in Fibroblasts from Gaucher Patients Isofagomine and derivatives IFG (33) is the most potent inhibitor tested for β-Glu in vitro. Its intracellular enhancement activity was investigated with fibroblasts established from a Gaucher patient with N370S/N370S genotype. The intracellular enzyme activity was increased 55-80% by cultivation the cell with IFG added in the culture medium at 1-50 μM (FIG. 8A). Higher than 50 μM concentration nullified the enhancement effect. The enhancement effect was monitored for 5 days. The residual enzyme activity in Gaucher cells did not change on day 1 or 2, however, the enzyme activity was elevated after day 3 and increased more than 80% at day 5 (FIG. 8B). This data demonstrated that IFG, a potent inhibitor of β-Glu, also serves as an enhancer for residual β-Glu in the cells derived from Gaucher patients when a appropriate concentration is applied. Effective concentrations are expected to be lower than those needed to inhibit the enzyme, but will be able to be determined through routine experimentation by those of skill in the art for Gaucher disease and other disorders. IFG derivatives (compounds 34-37) demonstrated significant impact on enhancement of the intracellular enzyme activity in Gaucher cells (N370S/N370S) cultivated with these compounds (FIG. 9). The residual enzyme activity was elevated 73% (compound concentration at 10 µM) and 56% (100 µM) by compound 34, 106% (10 µM) and 47% (100 µM) by compound 35, and 50% (10 µM) and 54% (100 µM) by compound 36, respectively. The residual enzyme activity was increased 43% by cultivation with compound 37 at 10 µM, however, decreased 53% with the compound at 100 µM. Although the inhibitory activity of the IFG derivatives was weaker than IFG, the intracellular enhancement activity of the IFG derivatives appears to be higher than IFG, since they achieved higher elevation of the mutant enzyme activity at lower concentrations. It is believed that the bioavailability of these compounds is significantly improved by the hydrophobic nature of the molecule, leading to easier crossing of cell and the ER membranes, thereby increasing the intracellular concentration of these compounds. Particularly, compound 37 at 100 µM decreased the residual activity, presumably intracellular concentration reached to the concentration required for inhibition.

N-dodecyl-DNJ N-dodecyl-DNJ (31) is one of the most potent inhibitors of β-Glu tested, and is believed to be recognized by the domain usually recognizing ceramide of the natural substrate. N-dodecyl-DNJ also enhanced β-Glu activity in fibroblasts derived from Gaucher patient with N370S/N370S mutation. The enzyme activity increased 95% by cultivation the cells with N-dodecyl-DNJ at 0.5 µM for 5 days (FIG. 10A). The elevation of enzyme activity was dose-dependent between the concentrations of 0.05-0.5 µM added to the medium. However, N-dodecyl-DNJ at higher than 1 µM nullified the enhancement effect. The time course of cultivation of the cells with N-dodecyl-DNJ at 0.5 µM indicated that the residual enzyme activity increased after day 3 (FIG. 10B). Since N-dodecyl-DNJ and IFG are recognized by different recognition domains of the enzyme (N-dodecyl-DNJ, ceramide recognition domain vs. IFG, glucoside recognition domain), a compound with a combination of N-dodecyl-DNJ and IFG such as N-dodecyl-IFG is expected to be a powerful agent for enhancing residual enzyme activity in Gaucher cells.

Calystegine compounds Calystegine $A_3$ (17), calystegine $B_1$ (23), calystegine $B_2$ (18) and calystegine $C_1$ (26) exhibited potent inhibitory activity against β-Glu and were tested for intracellular enhancement of β-Glu activity with fibroblasts derived from Gaucher patient with a genotype of L444P/L444P (FIG. 11). The residual enzyme activity in the patient's cells was increased 230%, 76%, 126% and 136% by cultivation with calystegine $B_2$, $B_1$, $A_3$ and $C_1$ at 10 µM, respectively. The results indicate that these compounds also act as effective enhancers for Gaucher fibroblasts.

Applicants have shown that i) α-allo-HNJ (9), α-HGJ (10), β-1-C-butyl-DGJ (16), calystegine $A_3$ (17), calystegine $B_2$ (18), N-metyl calystegine $A_3$ (19), and N-methyl calystegine $B_2$ (20) are able to effectively increase the intracellular α-Gal A activity in Fabry lymphoblasts by cultivation the cells with the above individual compound in concentration ranges of 10-1000 µM; ii) DGJ (4) and 4-epi-isofagomine (21) are able to effectively enhance the intracellular β-Gal activity in $G_{M1}$-gangliosidosis fibroblasts by cultivation the cells with the above individual compound in concentration ranges of 50-500 µM; iii) Calystegine $B_2$ (18), calystegine $B_1$(23), calystegine $A_3$ (17), calystegine $C_1$ (26), N-dodecyl-DNJ (31), isofagomine (33), N-butyl-isofagomine (34), N-(3-cyclohexylpropyl)-isofagomine (35), N-(3-phenylpropyl)-isofagomine (36) and N-[(2E,6Z,10Z)-3,7,11-trimethyldodecatrienyl]-isofagomine (37) are able to effectively enhance the intracellular β-Glu activity in Gaucher fibroblasts by cultivation the cells with the above individual compound in concentration ranges of 0.05-100 µM.

Applicants earlier disclosed in U.S. application Ser. No. 09/087,804 a method for treatment of Fabry disease by administration of potent competitive inhibitors of α-Gal A to enhance the intracellular α-Gal A activity in the Fabry lymphoblsts. The mechanism underlying this treatment is believed to be that the competitive inhibitors serve as chemical chaperones to induce/ensure the proper (native) conformation of the mutant protein for a smooth escape from the ER quality control system, thus accelerate the maturation and transport leading to increase of the intracellular enzyme activity. In the present application, Applicants further demonstrate the correlation between in vitro inhibition and intracellular enhancement with a series of inhibitors for α-Gal A. The results clearly show that more potent competitive inhibitors serve as more powerful enhancers for the mutant enzyme.

In the present application, it is demonstrated that the method for treatment of Fabry disease by administration of potent competitive inhibitor of the defective enzyme can be applied to $G_{M1}$-gangliosidosis and Gaucher disease, both diseases belong to lysosomal storage disorder family, and potent inhibitors for β-Gal or β-Glu can effectively enhance the intracellular enzyme activities in the fibroblasts established from patients of $G_{M1}$-gangliosidosis or Gaucher disease, respectively. Since the lysosomal storage disorders share the same biological and biochemical pathogenic mechanisms, this method of using potent competitive inhibitors of the defective enzyme is expected to be applicable for the treatment of other lysosomal storage disorders listed in Table 1.

Recent study on glycosidase inhibitors showed that conventional type of iminosugars having a nitrogen atom replacing the ring oxygen of a sugar such as 1-deoxynojirimycin are more potent and selective inhibitors for α-glycosidases, whereas 1-N-iminosugars having a nitrogen atom at the anomeric position of the pyranose ring are more potent and selective for β-glycosidases (40). We expect that conventional type of iminosugars (nojirimycin type), e.g., 1-deoxynojirimycin, 1-deoxy-galactonojirimycin, 1-deoxy-iduronojirimycin, 1,2-didcoxy-2-N -acetamido-nojirimycin, 1-deoxymannonojirimycin, 1-deoxyfuconojirimycin, 2,6-dideoxy-2,6-imino-sialic acid, and 1,2-dideoxy-2-N-acetamido-galactonojirimycin (FIG. 12), which have a ground-state structure of the substrate of a defective enzyme, e.g., α-glucosidase, α-galactosidase, α-L-iduronidase, α-N-acetylglucosaminidase, α-mannosidase, α-L-fucosidase, α-N-acetyl-neuraminidase, and α-N-acetylgalactosaminidase, are potent inhibitors and powerful enhancers for treatment of Pompe disease, Fabry disease, Hurler-Scheie disease, Sanfilippo disease, α-mannosidosis, Fucosidosis, Sialidosis and Schindler-Kanzaki disease, respectively. We also expect that 1-N-iminosugars, e.g., isofagomine, 4-epi-isofagomine, 2-N-acetamido-isofagomine, 6-carboxy-isofagomine, and 2-hydroxy-isofagomine (FIG. 12), which have a ground-state structure of the substrate of a defective enzyme, e.g., β-glucosidase, β-galactosidase, β-N-acetylglucosaminidase, β-glucuronidase and β-mannosidase, are potent inhibitors and powerful enhancers for treatment of Gaucher disease, $G_{M1}$-gangliosidosis, Krabbe disease, Morquio disease, Tay-Sachs disease, Sandohoff disease, Sly disease, and β-mannosidosis. A summary of potent competitive inhibitors which are expected to effectively enhance the mutant enzyme activity associated with lysosomal storage disorders is presented in Table 4.

TABLE 4

Summary of expected enhancers for lysosomal storage disorders.

| Disorder | Targeting enzyme | Enhancer | Ref. |
|---|---|---|---|
| Pompe disease | α-glucosidase | 1-deoxynojirimycin (DNJ) | 28 |
| | | α-homonojirimycin | 31 |
| | | castanospermine | *11 |
| Gaucher disease | Acid β-glucosidase, or glucocerebrosidase | isofagomine | 40 |
| | | N-dodecyl-DNJ | *1 |
| | | calystegines $A_3$, $B_1$, $B_2$, $C_1$ | *1 |
| Fabry disease | α-galactosidase A | 1-deoxygalactonojirimycin | 24 |
| | | α-allo-homonojirimycin | *2 |
| | | α-galacto-homonojirimycin | *2 |
| | | β-1-C-butyl-deoxynojirimycin | *2 |
| | | calystegines $A_3$, $B_2$ | *1 |
| | | N-methyl calystegines $A_3$, $B_2$ | *1 |
| $G_{M1}$-gangliosidosis | Acid β-galactosidase | 4-epi-isofagomine | *1 |
| | | 1-deoxygalactonojirimycin | *1 |
| Krabbe disease | Galactocerebrosidase | 4-epi-isofagomine | 40 |
| | | 1-deoxygalactonojirimycin | 28 |
| Morquio disease B | Acid β-galactosidase | 4-epi-isofagomine | 40 |
| | | 1-deoxygalactonojirimycin | 28 |
| α-Mannosidosis | Acid α-mannosidase | 1-deoxymannojirimycin | 40 |
| | | Swainsonine | *3 |
| | | Mannostatin A | *4 |
| β-Mannosidosis | Acid β-mannosidase | 2-hydroxy-isofagomine | 40 |
| Fucosidosis | Acid α-L-fucosidase | 1-deoxyfuconojirimycin | *5 |
| | | β-homofuconojirimycin | *5 |
| | | 2,5-imino-1,2,5-trideoxy-L-glucitol | *5 |
| | | 2,5-dideoxy-2,5-imino-D-fucitol | *5 |
| | | 2,5-imino-1,2,5-trideoxy-D-altritol | *5 |
| Sanfilippo disease B | α-N-Acetylglucosaminidase | 1,2-dideoxy-2-N-acetamido-nojirimycin | 40 |
| Schindler-Kanzaki disease | α-N-acetylgalactosaminidase | 1,2-dideoxy-2-N-acetamido-galactonojirimycin | 40 |
| Tay-Sachs disease | β-Hexosaminidase A | 2-N-acetylamino-isofagomine | 40 |
| | | 1,2-dideoxy-2-acetamido-nojirimycin | *6 |
| | | nagstain and its derivatives | *7, *8 |
| Sandhoff disease | β-Hexosaminidase B | 2-N-acetamido-isofagomine | 40 |
| | | 1,2-dideoxy-2-acetamido-nojirimycin | *6 |
| | | nagstain and its derivatives | *7, *8 |
| Hurler-Scheie disease | α-L-Iduronidase | 1-deoxyiduronojirimycin | 40 |
| | | 2-carboxy-3,4,5-trideoxypiperidine | *9 |
| Sly disease | β-Glucuronidase | 6-carboxy-isofagomine | 40 |
| | | 2-carboxy-3,4,5-trideoxypiperidine | *9 |
| Sialidosis | Sialidase | 2,6-dideoxy-2,6-imino-sialic acid | 40 |
| | | Siastatin B | *10 |

References:
*1, This application.
*2, Asano, N., Ishii, S., Kizu, H., Ikeda, K., Yasuda, K., Kato, A., Martin, O. R., and Fan, J. -Q. (2000) In vitro inhibition and intracellular enhancement of lysosomal α-galactosidase A activity in Fabry lymphoblasts by 1-deoxygalactonojirimycin and its derivatives. Eur. J. Biochem., in press.
*3, Dorling, P. R., Huxtable, C. R., and Colegate, S. M. (1980) Inhibition of lysosomal α-mannosidase by swainsonine isolated from *Swainsona canescens*. Biochem. J. 191, 649-651.
*4, Aoyagi, T., Yamamoto, T., Kojiri, K., Morishima, H., Nagai, M., Hamada, M., Takeuchi, T., and Umezawa, H., (1989) Mannostatins A and B: new inhibitors of alpha-D-mannosidase, produced by *Streptoverticillium verticillus* var. *quintum* ME3-AG3: taxonomy, production, isolation, physico-chemical properties and biological activities. J. Antibiot. 42, 883-889.
*5, Asano, N., Yasuda, K., Kizu, H., Kato, A., Fan, J. -Q., Nash, R. J., Fleet, G. W. J., and Molyneux, R. J. (2000) Novel α-L-fucosidase inhibitors from the bark of *Angylocalyx pynaertii* (Leguminosae). Submitted.
*6, Fleet, G. W. J., Smith, P. W., Nash, R. J., Fellows, L. E., Parekh, R. J., and Rademacher, T. W. (1986) Synthesis of 2-acetamido-1,5-imino-1,2,5-trideoxy-D-mannitol and of 2-acetamido-1,5-imino-1,2,5-trideoxy-D-glucitol, a potent and specific inhibitor of a number of β-N-acetylglucosaminidases. Chem. Lett. 1051-1054.
*7, Aoyagi T, Suda H, Uotani K, Kojima F, Aoyama T, Horiguchi K, Hamada M, Takeuchi T (1992) Nagstatin, a new inhibitor of N-acetyl-beta-D-glucosaminidase, produced by *Streptomyces amakusaensis* MG846-fF3. Taxonomy, production, isolation, physico-chemical properties and biological activities. J Antibiot (Tokyo) 45, 1404-8.
*8, Tatsuta K, Miura S, Ohta S, Gunji H (1995) Syntheses and glycosidase inhibiting activities of nagstatin analogs. J Antibiot (Tokyo) 48, 286-8.
*9, Cenci di Bello I, Dorling P, Fellows L, Winchester B (1984) Specific inhibition of human β-D-glucuronidase and α-L-iduronidase by a trihydroxy pipecolic acid of plant origin. FEBS Lett 176, 61-4.
*10, Umezawa H, Aoyagi T, Komiyama T, Morishima H, Hamada M (1974) Purification and characterization of a sialidase inhibitor, siastatin, produced by *Streptomyces*. J Antibiot (Tokyo) 27, 963-9.
*11, Pili R, Chang J, Partis RA, Mueller RA, Chrest FJ, Passaniti A (1995) The alpha-glucosidase I inhibitor castanospermine alters endothelial cell glycosylation, prevents angiogenesis, and inhibits tumor growth. Cancer Res 55, 2920-6.

References cited herein are hereby incorporated by reference and are listed beloved for convenience.
1. Anfinsen, C. B., Scheraga, H. A. (1975) Experimental and theoretical aspects of protein folding. *Adv. Protein Chem.* 29, 205-300.
2. Hartl, F. U. (1996) Molecular chaperones in cellular protein folding. *Nature* 381, 571-580.
3. Gething, M. J., Sambrook, J. (1992) Protein folding in the cell. *Nature* 355, 33-45.
4. Caplan, A. J. (1999) Hsp90's secrets unfold: New insights from structural and functional studies. *Trends Cell Biol.* 9, 262-268.
5. Lin, H., Masso-Welch, P., Di, Y. Cai, J. W., Shen, J. W. and Subjeck, J. R. (1993) The 170-kDa glucose-regulated stress protein is an endoplasmic reticulum protein that binds immunoglobulin. *Mol. Biol. Cell* 4, 1109-1119.

6. Bergeron, J. J. M., Brenner, M. B., Thomas, D. Y. and Williams, D. B. (1994) Calnexin: A membrane-bound chaperone of the endoplasmic reticulum. *Trends Biochem. Sci.* 19, 124-128.
7. Haas, I. G. (1991) Bip—a heat shock potein involved in immunoglobulin chain assembly. *Curr. Top Microbiol. Immunol.* 167, 71-82.
8. Hurtley, S. M., and Helenius, A. (1989) Protein oligomerization in the endoplasmic reticulum. *Annu. Rev. Cell Biol.* 5, 277-307.
9. Kuznetsov, G., and Nigam, S. K. (1998) Folding of secretory and membrane proteins. *N. Engl. J Med* 339, 1688-1695.
10. Thomas, P. J., Qu, B. H., and Pedersen, P. L. (1995) Defective protein folding as a basis of human disease. *Trends Biochem. Sci.* 20, 456-459.
11. Bychkova, V. E., and Ptitsyn, O. B. (1995) Folding intermediates are involved in genetic diseases? *FEBS Lett.* 359, 6-8.
12. Brooks, D. A. (1997) Protein processing: a role in the pathophysiology of genetics disease. *FEBS Lett.* 409, 115-120.
13. Yang, Y., Janich, S., Cohn, J. A., and Wilson, J. M. (1993) The common variant of cystic fibrosis transmembrane conductance regulator is recognized by hsp70 and degraded in a pre-Golgi nonlysosomal compartment. *Proc. Natl. Acad. Sci. USA* 90, 9480-9484.
14. Ward, C. L., Omura, S., and Kopito, R. R. (1995) Degradation of CFTR by the ubiquitin-proteasome pathway. *Cell* 83, 121-127.
15. Pasyk, E. A., and Foskett, J. K. (1995) Mutant ($\Delta$F508) cystic fibrosis transmembrane conductance regulator Cl⁻ channel is functional when retained in endoplasmic reticulum of mammalian cells. *J. Biol. Chem.* 270, 12347-12350.
16. Lomas D. A., Evans, D. L., Finch, J. T., and Carrell, R. W. (1992) The mechanism of Z $\alpha_1$-antitrypsin accumulation in the liver. *Nature* 357, 605-607.
17. Qu, D., Teckman, J. H., Omura, S., and Perlmutter, D. H. (1996) Degradation of a mutant secretory protein, $\alpha_1$-antitrypsin Z, in the endoplasmic reticulum requires proteasome activity. *J. Biol. Chem.* 271, 22791-22795.
18. Djordjevic, J. T., Bieri, S., Smith, R., and Kroon, P. A. (1996) A deletion in the first cysteine-rich repeat of the low-density-lipoprotein receptor leads to the formation of multiple misfolded isomers. *Eur. J. Biochem.* 239, 214-219.
18a. Selkoe, D. J. (1994) Normal and abnormal biology of the $\beta$-amyloid precursor protein. *Ann. Rev. Neurosci.* 17, 489-517.
19. Ramirez, F. (1996) Fibrillln mutations in Marfan syndrome and related phenotypes. *Curr. Opin. Genet. Dev.* 6, 309-315.
20. Chessler, S. D., and Byers, P. H. (1993) BiP binds type I procollagen pro alpha chains with mutations in the carboxyl-terminal propeptide synthesized by cells from patients with osteogenesis imperfecta. *J. Biol. Chem.* 268, 18226-18233.
21. Marquardt, T., Ullrich, K., Zimmer, P., Hasilik, A., Deufel, T., and Harms, E. (1995) Carbohydrate-deficient glycoprotein syndrome (CDGS)-glycosylation, folding and intracellular transport of newly synthesized glycoproteins. *Eur. J Cell. Biol.* 66, 268-273.
22. Bradford, T. M., Gething, M. J., Davey, R., Hopwood, J. J., and Brooks, D. A. (1999) Processing of normal lysosomal and mutant N-acetylgalactosamine 4-sulphatase: BiP (immunoglobulin heavy-chain binding protein) may interact with critical protein contact sites. *Biochem. J.* 341, 193-201.
23. Desnick, R. J., Ioannou, Y. A. and Eng, C. M. ∀-Galactosidase A deficiency: Fabry disease. in *The Metabolic and Molecular Bases of Inherited Disease* (eds. Scriver, C. R., Beaudet, A. L., Sly. W. S. and Valle, D.), 2741-2784 (McGraw-Hill, New York, 1995).
24. Fan, J.-Q., Ishii, S., Asano, N. and Suzuki, Y. (1999) Accelerated transport and maturation of lysosomal $\alpha$-galactosidase A in Fabry lymphoblasts by an enzyme inhibitor. *Nature Med.* 5, 112-115.
25. Ishii, S., Kase, R., Sakuraba, H., and Suzuki, Y. (1993) Characterization of a mutant $\alpha$-galactosidase gene product for the late-onset cardiac form of Fabry disease, *Biochem. Biophys. Res. Comm.* 197, 1585-1589.
25a. Leinekugel, P., Michel, S., Conzelmann, E., and Sandhoff, K. (1992) Quantitative correlation between the residual activity of beta-hexosaminidase A and arylsulfatase A and the severity of the resulting lysosomal storage disease. *Hum. Genet.* 88, 513-23.
25b. Kappler, J., Watts, R. W., Conzelmann, E., Gibbs, D. A., Propping, P., and Gieselmann, V. (1991) Low arylsulphatase A activity and choreoathetotic syndrome in three siblings: Differentiation of pseudodeficiency from metachromatic leukodystrophy. *Eur. J. Pediatr.* 150, 287-290.
26. Beutler, E., and Grabowski, G. A. Gaucher disease. in *The Metabolic and Molecular Bases of Inherited Disease* (eds. Scriver, C. R., Beaudet, A. L., Sly, W. S and Valle, D.), 2641-2670 (McGraw-Hill, New York, 1995).
27. Suzuki, Y., Sakuraba, H., and Oshima, A. $\beta$-Galactosidase deficiency ($\beta$-galactosidosis): $G_{M1}$-gangliosidosis and Morquio B disease. in *The Metabolic and Molecular Bases of Inherited Disease* (eds. Scriver, C. R., Beaudet, A. L., Sly, W. S. and Valle, D.), 2785-2824 (McGraw-Hill, New York, 1995).
28. Asano, N., Oseki, K., Tomioka, E, Kizu, H., and Matsui, K. (1994) N-containing sugars from *Morus alba* and their glycosidase inhibitory activities. *Carbohydr. Res.* 259, 243-255.
29. Asano, N., Oseki, K., Kizu, H., and Matsui, K. (1994) Nitrogen-in-the-ring pyranoses and furanoses: structural basis of inhibition of mammalian glycosidases. *J. Med. Chem.* 37, 3701-3706.
30. Heiker, F.-R. and Schueller, A. M. (1990) Synthesis of D-galacto-1-deoxynojirimycin (1,5-dideoxy-1,5-imino-D-galactitol) starting from 1-deoxynojirimycin. *Carbohydr. Res.* 203, 314-318.
31. Asano, N., Nishida, M., Kizu, H., and Matsui, K. (1997) Homonojirimycin isomers and glycosides from *Aglaonema treubii J. Nat. Prod.* 60, 98-101.
32. Martin, O. R., Compain, P., Kizu, H., and Asano, N. (1999) Revised structure of a homonojirimycin isomer from Aglaonema treubii: first example of a naturally occurring $\alpha$-homoallonojirimycin. *Bioorg. Med. Chem. Lett.* 9, 3171-3174.
33. Martin, O. R., Xie, F., and Liu, L. (1995) Synthesis of "$\alpha$-homogalactostatin" and of its 1,N-anhydro derivative. *Tetrahedron Lett.* 36, 4027-4030.
34. Kato, H., Koshinaka, E., Arata, Y., and Hanaoka, M. (1973) Studies on 1-azabicyclo compound. XVI. Synthesis of 1'-methylindan-2-spiro-2'-piperazine and related compounds. *Chem. Pharm. Bull.* 21, 2661-2666.
35. Ikeda, K., Takahashi, M., Nishida, M., Miyauchi, M., Kizu, H., Kameda, Y., Arisawa, M., Watson, A. A., Nash, R. J., Fleet, G. W. J., and Asano, N. (1999) *Carbohydr. Res.*, 323, 73-80.

36. Asano N, Kato A, Matsui K, Watson A A, Nash R J, Molyneux R J, Hackett L, Topping J, Winchester B (1997) The effects of calystegines isolated from edible fruits and vegetables on mammalian liver glycosidases. *Glycobiology* 7, 1085-8.
37. Ishii, S., Kase, R., Sakuraba, H., Fujita, S., Sugimoto, M., Tomita, K., Semba, T., and Suzuki, Y. (1 994) Human α-galactosidase gene expression: significance of two peptide regions encoded by exons 1-2 and 6. *Biochem. Biophys. Acta* 1204, 265-270.
38. Ishii, S., Kase, R., Sakuraba, H., and Suzuki, Y. (1993) Characterization of a mutant α-galactosidase gene product for the late-onset cardiac form of Fabry disease. *Biochem. Biophys. Res. Comm.* 197, 1585-1589.
39. Legler, G. and Pohl, S. (1986) Synthesis of 5-amino-5-deoxy-D-galactopyranose and 1,5-dideoxy-1,5-imino-D-galactitol, and their inhibition of α- and β-D-galactosidases. *Carbohydr. Res.* 155, 119-129.
40. Ichiwaka, Y., Igarashi, Y., Ichikawa, M, and Suhara, Y. (1998) 1-N-Iminosugars: Potent and selective inhibitors of β-glycosidases. *J. Am. Chem. Soc.* 120, 3007-3018.
40a. Asano, N., Kato, A., Oseki, K., Kizu, H., and Matsui, K. (1995) Calystegins of *Physalis alkekengi* var. francheti (Solanaceae). Structure determination and their glycosidase inhibitory activities. *Eur. J. Biochem.* 229, 369-76.
41. Junge, B., Matzke, M., and Stoltefuss, J. (1996) Chemistry and structure-activity relationships of glucosidase inhibitors. in *Handbook of Experimental Pharmacology* (Born, G. V. R., Cuatrecasas, P., Herken, H., and Melmon, K. L., eds) Vol. 119, pp. 411-482, Springer-Verlag, Berlin Heiderberg.
42. Schweden, J., Boegmann, C., Legler, G., and Bause, E. (1986) Characterization of calf liver glucosidase I and its inhibition by basic sugar analogs. *Arch. Biochem. Biophys.* 248, 335-340.
43. Tan, A., van den Broek, L., van Boeckel, S., Ploegh, H., and Bolscher, J. (1991) Chemical modification of the glucosidase inhibitor 1-deoxynojirimycin. Structure-activity relationships *J. Biol. Chem.* 266, 14504-14510.
44. Zeng, Y., Pan, Y. T., Asano, N., Nash, R., and Elbein, A. D. (1997) 1-Homonojirimycin and N-methyl-homonojirimycin inhibit N-linked oligosaccharide processing. *Glycobiology* 7, 297-304.
45. Platt, F. M., Neises, G. R., Dwek, R. A., and Butters, T. D. (1994) N-butyldeoxynojirimycin is a novel inhibitor of glycolipid biosynthesis. *J. Biol. Chem.* 269, 8362-8365.
46. Platt, F. M., Neises, G. R., Karlsson, G. B., Dwek, R. A., and Butters, T. D. (1994) N-butyldeoxygalactonojirimycin inhibits glycolipid biosynthesis but does not affect N-linked oligosaccharide processing. *J. Biol. Chem.* 269, 27108-27114.
47. Molyneux, R. J., Nash, R. J. and Asano, N. (1996) The chemistry and biology activity of calystegines and related nortropane alkaloids. In *Alkaloids: chemical and biological Perspective, Vol* 11 (Pelletier, S. W., ed.) pp 303-343. Elsevier Science, Oxford.

What is claimed:

1. A method for increasing in a mammalian cell the activity of acid-β-galactosidase, which method comprises contacting the cell with a reversible competitive inhibitor of the acid-β-galactosidase in an amount effective to increase acid-β-galactosidase activity.

2. The method of claim 1, wherein the competitive inhibitor is selected from the group consisting of 4-epi-isofagomine and 1-deoxygalactonojirimycin.

3. The method of claim 2, wherein the competitive inhibitor is 1-deoxygalactonojirimycin.

4. The method of claim 2, wherein the competitive inhibitor is 4-epi-isofagomine.

* * * * *